(12) United States Patent
Nakatani et al.

(10) Patent No.: US 8,030,059 B2
(45) Date of Patent: *Oct. 4, 2011

(54) APPARATUS FOR MEASURING EXTRACELLULAR POTENTIAL

(75) Inventors: Masaya Nakatani, Hyogo (JP); Nobuhiko Ozaki, Nara (JP); Hiroaki Oka, Osaka (JP)

(73) Assignee: Panasonic Corporation, Osaka (JP)

( * ) Notice: Subject to any disclaimer, the term of this patent is extended or adjusted under 35 U.S.C. 154(b) by 689 days.

This patent is subject to a terminal disclaimer.

(21) Appl. No.: 12/133,461

(22) Filed: Jun. 5, 2008

(65) Prior Publication Data

US 2008/0257727 A1 Oct. 23, 2008

Related U.S. Application Data

(62) Division of application No. 10/991,269, filed on Nov. 17, 2004, now Pat. No. 7,396,673.

(30) Foreign Application Priority Data

Nov. 21, 2003 (JP) ................................. 2003-392220

(51) Int. Cl.
*C12M 1/34* (2006.01)
(52) U.S. Cl. ............... 435/287.1; 435/285.2; 435/288.5; 435/293.1; 435/293.2; 435/305.2; 204/403.01; 205/777.5
(58) Field of Classification Search ............... 435/287.1, 435/285.2, 288.5, 293.1, 293.2, 305.2; 204/403.01; 205/777.5
See application file for complete search history.

(56) References Cited

U.S. PATENT DOCUMENTS

| 5,183,744 | A | 2/1993 | Kawamura et al. |
| 5,563,067 | A * | 10/1996 | Sugihara et al. ........... 435/287.1 |
| 5,569,591 | A | 10/1996 | Kell et al. |
| 6,063,260 | A | 5/2000 | Olesen et al. |
| 6,163,719 | A | 12/2000 | Sherman |
| 6,682,649 | B1 | 1/2004 | Petersen et al. |
| 6,984,297 | B2 | 1/2006 | Nisch et al. |
| 7,006,929 | B2 | 2/2006 | Oka et al. |
| 7,396,673 | B2 * | 7/2008 | Nakatani et al. ........... 435/287.1 |
| 2002/0074227 | A1 | 6/2002 | Nisch et al. |
| 2003/0107386 | A1 | 6/2003 | Dodgson et al. |

(Continued)

FOREIGN PATENT DOCUMENTS

EP  0 689 051 A2  12/1995

(Continued)

OTHER PUBLICATIONS

Partial European Search Report for EP 04 02 7447, dated Feb. 17, 2005.

(Continued)

*Primary Examiner* — William H Beisner
(74) *Attorney, Agent, or Firm* — RatnerPrestia

(57) ABSTRACT

A sensing element for measuring extracellular potential including a substrate, a well provided in a substrate, a guide section provided on the wall of the well, and a detective electrode formed at a lower surface of the substrate. The guide section is for guiding drug. The well is provided at the bottom with a depression, and a first throughhole penetrating through the depression and the lower surface of the substrate. The well is for mixing a subject cell, a culture solution and the drug together. The above-configured sensing element accurately measures a change generated by a subject cell.

14 Claims, 22 Drawing Sheets

U.S. PATENT DOCUMENTS

| | | |
|---|---|---|
| 2003/0113833 A1 | 6/2003 | Oka et al. |
| 2004/0033483 A1 | 2/2004 | Oka et al. |
| 2004/0197898 A1 | 10/2004 | Nakatani et al. |
| 2005/0221469 A1 | 10/2005 | Nakatani et al. |

FOREIGN PATENT DOCUMENTS

| | | |
|---|---|---|
| EP | 0 652 308 B1 | 3/2002 |
| EP | 1 203 823 | 5/2002 |
| EP | 1 352 952 A1 | 10/2003 |
| EP | 1 533 615 A2 | 5/2005 |
| JP | 2-131569 A | 5/1990 |
| JP | 6-244257 A | 9/1994 |
| JP | 2003-511668 A | 3/2003 |
| JP | 2003-511699 A | 3/2003 |
| JP | 2004-271330 A | 9/2004 |
| JP | 2004-271331 A | 9/2004 |
| JP | 2010-186807 | 3/2011 |
| WO | WO 99/31503 | 6/1999 |
| WO | WO 99/32881 | 7/1999 |
| WO | WO 00/34776 | 6/2000 |
| WO | WO 01/25769 A2 | 4/2001 |
| WO | WO 02/055653 A1 | 7/2002 |
| WO | WO 02/065092 A2 | 8/2002 |
| WO | WO 02/099408 A1 | 12/2002 |
| WO | WO 03/016555 A1 | 2/2003 |
| WO | WO 2004/079354 A1 | 9/2004 |

OTHER PUBLICATIONS

European Search Report for EP 04 02 7447, dated Apr. 13, 2005.
European Search Report for Application No. EP 07 11 6970, dated Nov. 2, 2007.
European Search Report for Application No. EP 07 11 6972, dated Nov. 15, 2007.

* cited by examiner

APPARATUS FOR MEASURING EXTRACELLULAR POTENTIAL

This application is a divisional of U.S. patent application Ser. No. 10/991,269, filed Nov. 17, 2004, which is U.S. Pat. No. 7,396,673, issued Jul. 8, 2008, the entire disclosure of which is incorporated herein by reference.

BACKGROUND OF THE INVENTION

1. Field of the Invention

The present invention relates to an extracellular potential sensing element and a device for measuring an extracellular potential, which are used for performing simply and quickly the electrophysiological evaluation of a biological sample, such as a cell, using an electrochemical change generated by the biological sample as an index. The present invention relates also to an apparatus for measuring extracellular potential, and a method of measuring extracellular potential by using the same.

2. Background Art

Drug screening has been conducted using the electrical activity of a cell as an index. Conventionally, the electrical activity of a cell is measured by a patch clamp technique or a technique employing a fluorescent pigment, or a light emitting indicator.

In a patch clamp technique, a small portion (hereinafter referred to as "patch") of cell membrane is attached to a tip portion of a micropipette, and is used to electrically record with a microelectrode probe the ion transport through a single ion channel protein. The patch clamp technique is one of a few-number of cell biological techniques which can be used to investigate the function of a single protein in real time.

In the other technique, a light generated in response to a change in the concentration of a particular ion is monitored employing a fluorescent pigment, or a light emitting indicator, for measuring the electrical activity of a cell (hereinafter referred to as "fluorescence measuring technique").

The patch clamp technique requires special techniques for preparation, manipulation and the like of a micropipette, and much time for measuring one sample. Therefore, the patch clamp technique is not suitable for screening a large quantity of candidate compounds for a drug at high speed.

The fluorescence measuring technique can screen a large quantity of candidate compounds for a drug at high speed. However, the fluorescence measuring technique requires a step of staining a cell. During measurement, pigments cause high background noise, and the fluorescence intensity decreases with time, resulting in poor signal to noise ratio (S/N).

An alternative method has been disclosed in WO 02/055653 (hereinafter referred to as "patent document 1"); that is a method of measuring extracellular potential (hereinafter referred to as "extracellular potential measuring method"). The extracellular potential measuring method offers data of high quality level comparable to those by patch clamp technique. Furthermore, the extracellular potential measuring method can measure a large quantity of samples at high speed by a simple process, as the fluorescence measuring technique does.

Patent document 1 discloses an extracellular potential measuring device (hereinafter referred to as "device"), which measures extracellular potential or physicochemical change generated by a cell. The device includes at least one well having means for holding a cell provided on a substrate. The well has a sensing means for detecting an electrical signal.

FIG. 40 illustrates the structure of a typified conventional extracellular potential measuring device. Culture solution 110 is in well 103. Subject cell (cell) 105 is captured or held by cell holding section 113 provided on substrate 102. Cell holding section 113 is formed of depression 104, opening section 106 and throughhole 107 in substrate 102. Throughhole 107 is connected to depression 104 via opening section 106. Detective electrode 109, or sensing means, is disposed in throughhole 109, and detective electrode 109 is connected with a signal detection section (not shown) via wire 108.

During the measurement, cell 105 is sucked by a sucking pump (not shown), or the like means, from the throughhole 107 side, so that it is held to be close to depression 104. At the same time, culture solution 110 flows to the throughhole 107 side and makes contact with detective electrode 109. Thus, an electrical signal generated as the result of activity of cell 105 is detected by detective electrode 109 disposed at the throughhole 107 side, with no leakage into culture solution 110 in well 103.

In the measuring method using a conventional extracellular potential measuring device, cell 105 is reacted with drug (not shown). Therefore, drug needs to be injected into culture solution 110. The injection of drug into culture solution 110 inevitably causes a flow of culture solution 110 in the neighborhood of cell 105. If the change in flow with culture solution 110 is substantial in the neighborhood of cell 105, fluctuation arises with culture solution 111 which is making contact with detective electrode 109. The fluctuation arising in culture solution 111 becomes noise to detecting by detective electrode 109.

In measuring the extracellular potential, the noise to detecting by detective electrode 109 is a cause that deteriorates the S/N ratio of a signal detected by detective electrode 109. Noise is caused by fluctuation of culture solution 111 has a low frequency, approximately 100 Hz or lower. While, the change in extracellular potential exhibits DC signal or a signal that changes with a cycle of less than approximately 5 kHz. Namely, the two signals share an overlapping frequency range.

It has been tried to reduce the noise by means of an electrical filter or the like, but it also cuts off the signal of low frequency region close to DC signal. In some cases, depending on the filter characteristics, even a higher frequency signal of 100 Hz is cut off either. Consequently, it is difficult to detect accurately a signal which represents extracellular potential generated by cell 105.

SUMMARY OF THE INVENTION

A sensing element for measuring extracellular potential in accordance with the present invention has a substrate, a well provided in the substrate, a guide section provided on the wall of the well, and a detective electrode disposed at a lower surface of the substrate. The guide section is for guiding drug. The well is provided at the bottom with a depression, and a first throughhole penetrating through the depression and the lower surface of the substrate. The well is for mixing a subject cell, a culture solution and the drug together.

DETAILED DESCRIPTION OF INVENTION

First Embodiment

Figure 1:
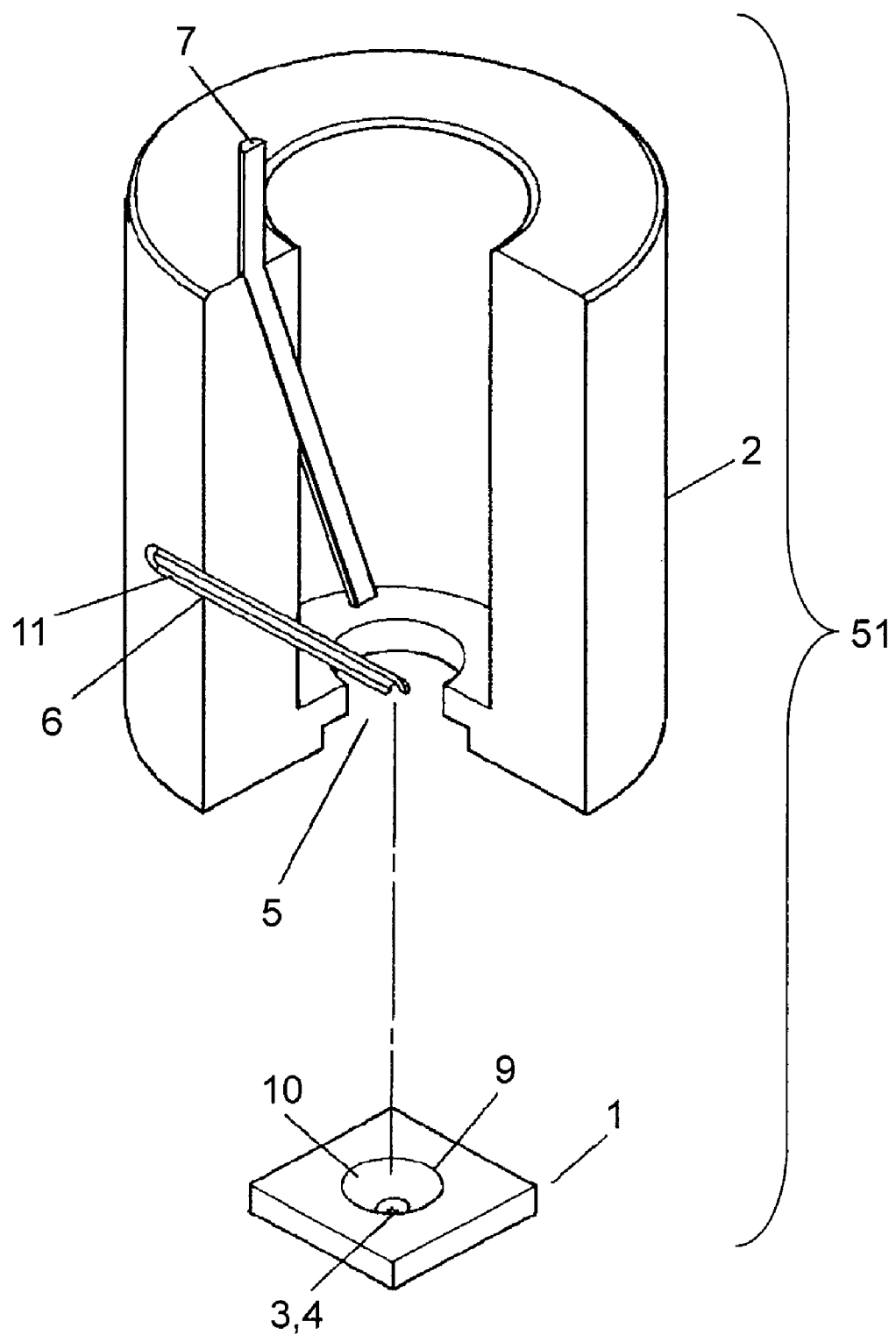
FIG. 1 is a partially-cut-off and exploded perspective view showing an extracellular potential measuring device in accordance with a first exemplary embodiment of the present invention.
Figure 2:
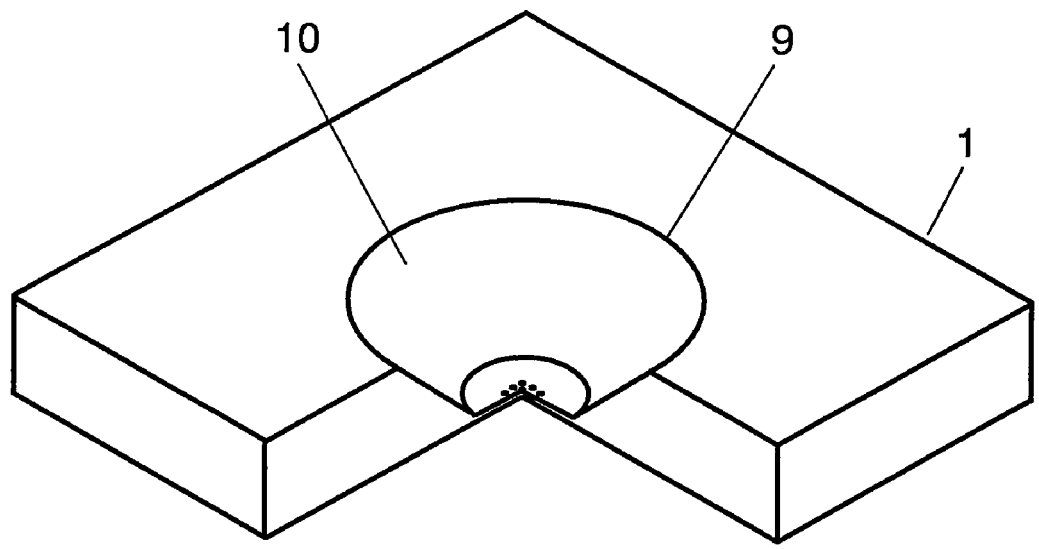
FIG. 2 is a partially-cut-off perspective view showing a sensing element used in the measuring device of FIG. 1.
Figure 3:
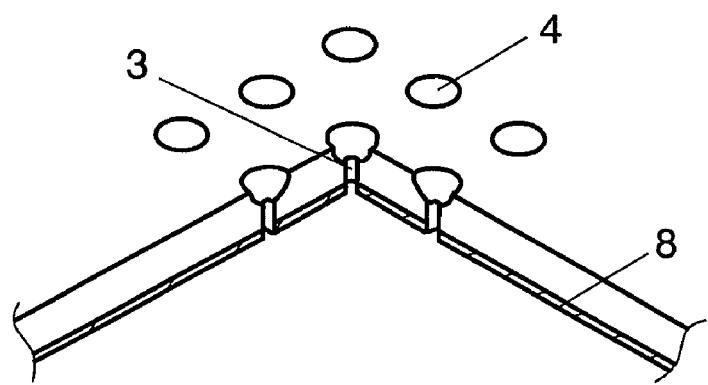
FIG. 3 is a partially-cut-off and magnified perspective view showing a key portion of the sensing element of FIG. 2.

FIG. 1 is a partially-cut-off and exploded perspective view of an extracellular potential measuring device in accordance with a first embodiment; case of which device is partly cut-off in order to show the inside. FIG. 2 is a partially-cut-off perspective view of a sensing element for measuring extracellular potential (hereinafter referred to as "sensing element"). FIG. 3 is a partially-cut-off and magnified perspective view showing a key portion of the sensing element of FIG. 2.

Extracellular potential measuring device (device) 51 is formed of case 2 and extracellular potential measuring sensing element 1 attached thereto. Sensing element 1 is a lamination of silicon and silicon dioxide. Case 2 is made of an electrically insulating resin material, and provided with reference electrode 7 for measuring the potential within case 2.

Sensing element 1 is provided with well 9 which have the opening at the upper surface of sensing element 1. At the bottom of well 9, first micro-throughhole (throughhole) 3 and depression 4 are provided. Throughhole 3, diameter of which is smaller than that of depression 4, is penetrating through the bottom surface of depression 4 and the lower surface of sensing element 1. Sensing element 1 is provided at the lower surface with detective electrode 8, as shown in FIG. 3. Detective electrode 8 is located in a bottom end of throughhole 3.

Case 2 has second throughhole (throughhole) 5 provided at the bottom. Size of throughhole 5 is larger than that of the opening of well 9. Wall 10 of well 9 has a bowl shape, and is for keeping culture solution and drug.

Case 2 is provided in the side wall with third throughhole (throughhole) 6. Tube 11 is inserted in throughhole 6. Tube 11 is guided by throughhole 6 so that a tip-end of tube 11 is accurately positioned on the place of throughhole 3 and depression 4.

Figure 5:
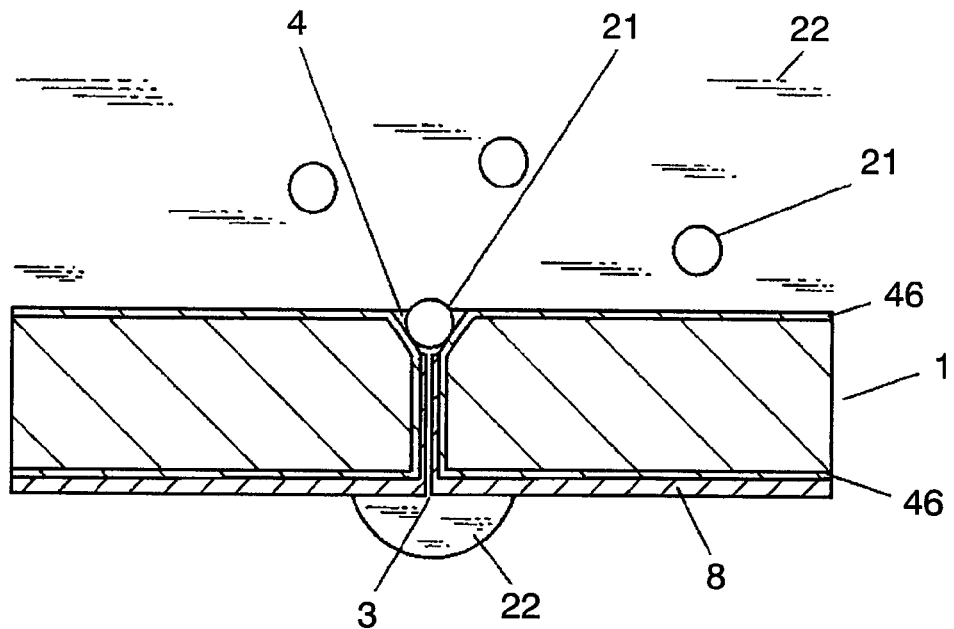
FIG. 5 is a magnified cross sectional view showing the device of FIG. 1.
Figure 6:
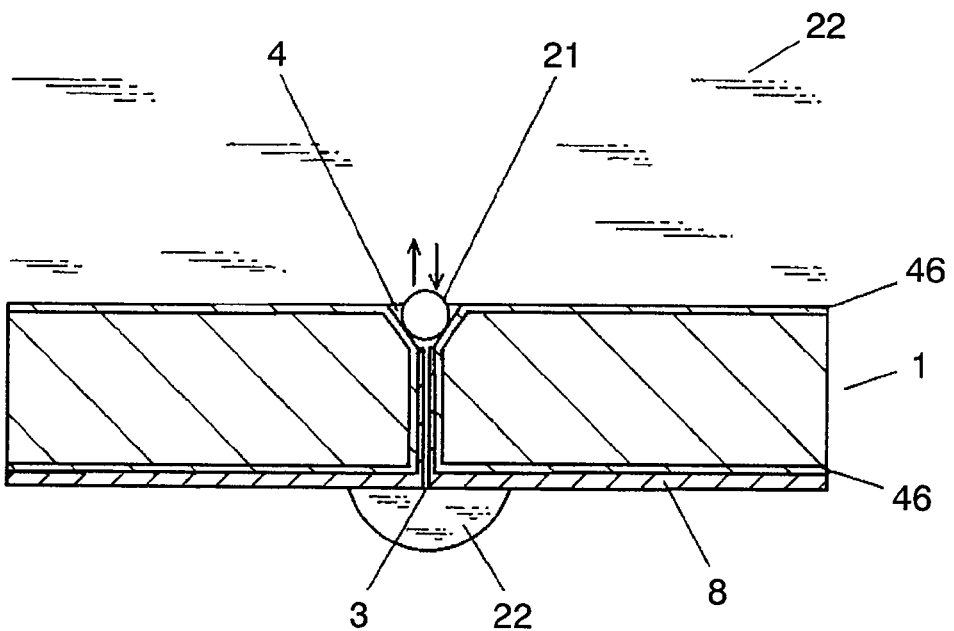
FIG. 6 is a magnified cross sectional view showing the device of FIG. 1.

FIG. 5 and FIG. 6 illustrate that the surfaces of depression 4 and throughhole 3 are covered with oxide layer 46. Oxide layer 46 is formed depending on needs, in accordance with kind, size, etc. of a subject cell. Oxide layer 46 varies in the thickness; it may have a thickness of 10000 angstrom or more when it is formed through thermal oxidation, while it may have a thickness of 500 angstrom or less when it is formed naturally. The thickness of oxide layer 46 is not an essential condition to the present invention.

Next, a method how to use measuring device 51 is described.

Figure 4:
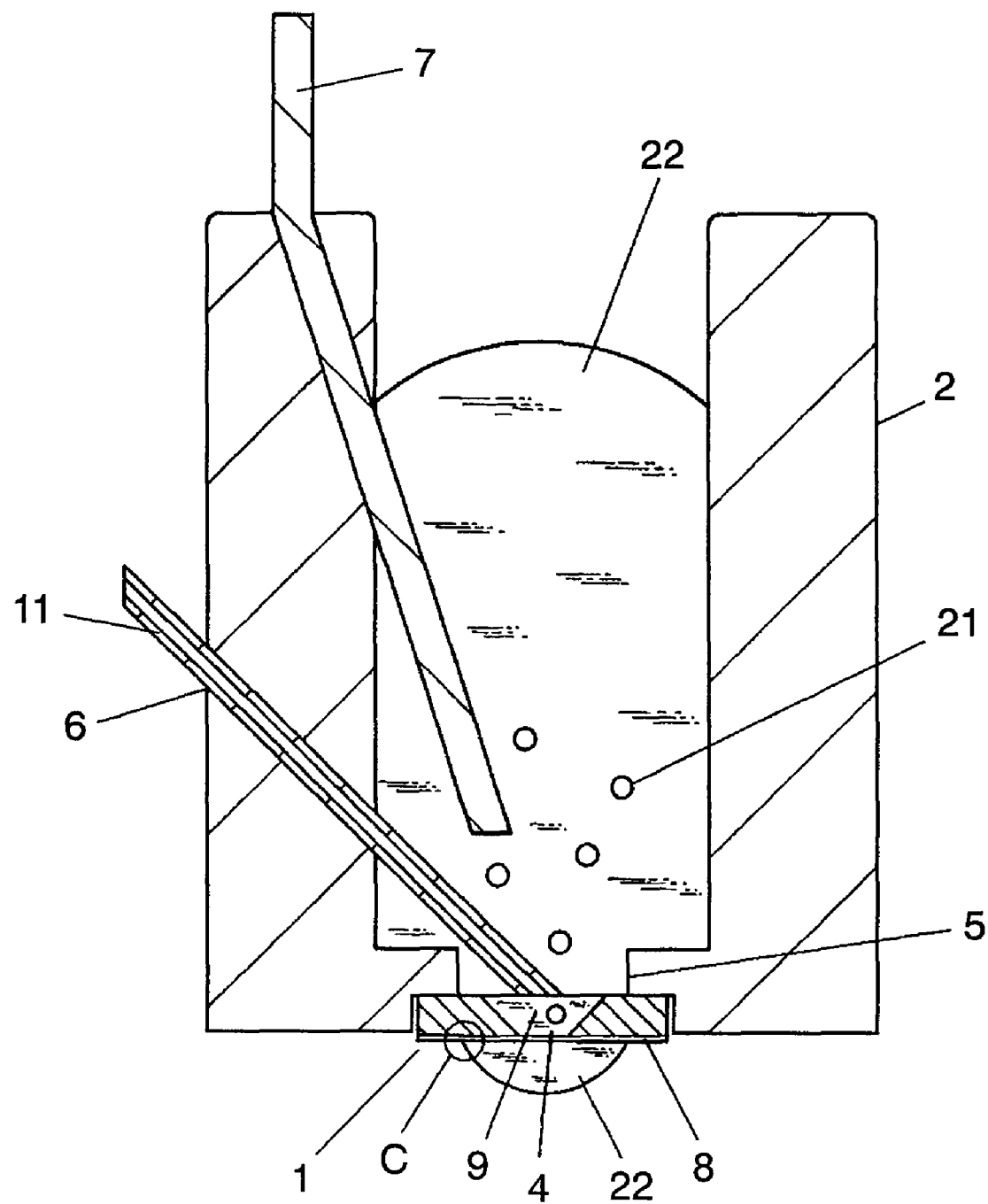
FIG. 4 is a cross sectional view used to show how to use the device of FIG. 1.

FIG. 4 is a cross sectional view used to show how to use measuring device 51. FIG. 5 and FIG. 6 show magnified cross sectional views of throughhole 3 and depression 4.

When culture solution 22 and subject cell (cell) 21 are put into case 2, cell 21 drifts in culture solution 22. Inside of case 2, depression 4 and throughhole 3 are filled with culture solution 22, and then culture solution 22 flows out into the side of detective electrode 8.

Cell 21 drifting in culture solution 22 flows due to a pressure within case 2, and sucked into depression 4, as shown in FIG. 5 and FIG. 6. If a pressure for sucking cell 21 is not high enough, a suction pump (not shown) or the like means is used to pull culture solution 22 from the detective electrode 8 side. Then, cell 21 drifting in culture solution 22 is surely pulled towards depression 4. Since the size of throughhole 3 has been designed to be smaller than that of cell 21, cell 21 is retained to be staying within the inside of depression 4.

Figure 7:
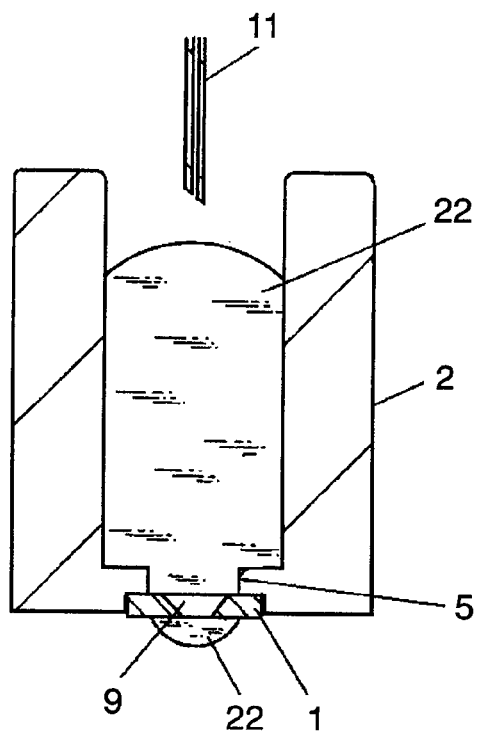
FIG. 7 is a cross sectional view showing the device of FIG. 1.
Figure 8:
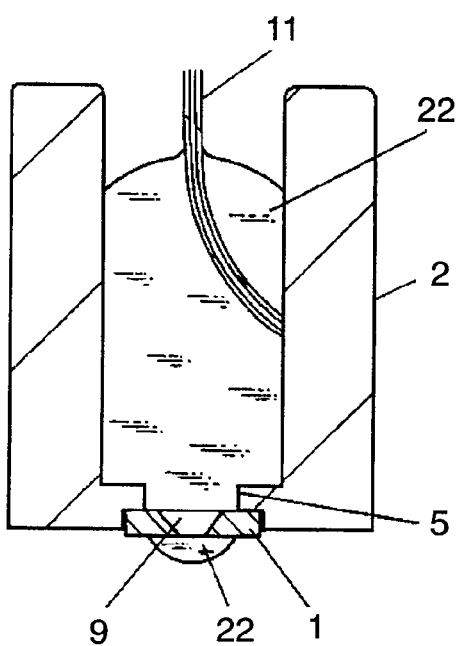
FIG. 8 is a cross sectional view showing the device of FIG. 1.

Meanwhile, in order to have drug (not shown) dispensed in the neighborhood of cell 21 without fail, arranging the tip-end of tube 11 needs to be placed as close to depression 4, where cell 21 is held. Since normally-used tube 11 is as fine as 1 mm or less in the diameter, tube 11 can easily be bent due to the surface tension of culture solution 22 when tube 11 is put into case 2 filled with culture solution 22 from the above, as shown in FIG. 7 and FIG. 8. So, it is not an easy task to locate the tip-end of tube 11 accurately at a certain specified location.

Therefore, throughhole 6 that radiates from a location where throughhole 3 and depression 4 are placed is provided in the side wall of case 2. Tube 11 is inserted in throughhole 6. Thus the tip-end of tube 11 can be positioned accurately to be very close to throughhole 3 and depression 4.

As described above, tip-end of tube 11 can be located easily at a certain specified location without being ill-affected by the surface tension of culture solution 22 which is filling case 2. Namely, the wall surface of throughhole 6 serves as the guide for tube 11. Thus, drug can be dispensed at any time in a stable manner.

Since wall 10 is bowl-shaped, the drug can easily be injected into the inside of well 9. Therefore, even if a pressure of dispensing the drug through tube 11 is low, the drug can surely make a reach to the neighborhood of cell 21 which is held at depression 4. Cell 21 would not be stressed inadvertently, and a resultant vibration which could be caused by a pressurized cell 21 can be prevented. The bowl-shaped wall 10 functions as a guide section for guiding drug into well 9.

Since throughhole 5 is designed to be larger than the opening of well 9, lower side of case 2 does not cover the bowl contour of well 9. So, the drug can easily be injected into the bottom part of well 9.

Preferably, tube 11 is made of a material selected from the group consisting of a resin, a glass and silica. These materials are electrically insulating, so insertion of such a material into case 2 would not invite a disturbance with the potential of culture solution 22 inadvertently.

Figure 9:
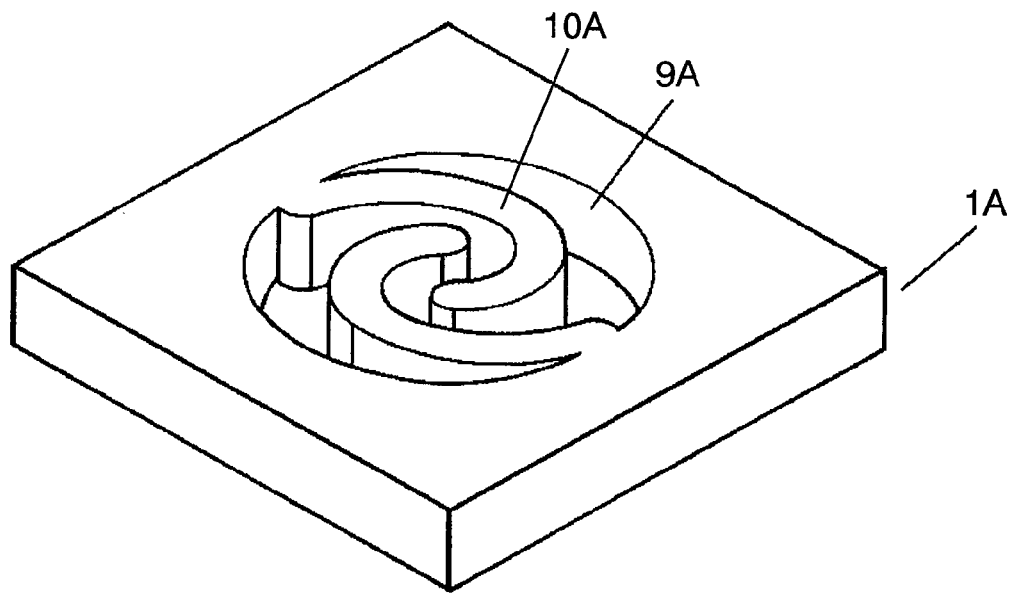
FIG. 9 is a perspective view of a sensing element used in the device of FIG.

Next, as shown in FIG. 9, wall 10A of well 9A may be formed in a spiral-shape. The spiral-shape of wall 10A facilitates homogeneous mixing of the dispensed drug with culture solution 22 kept in well 9A, even when a low dispensing pressure is injected for the drug and the speed of inflow is low. Sensing element 1A having spiral wall 10A is advantageous in performing high accuracy measurements with a least spread.

Figure 10:
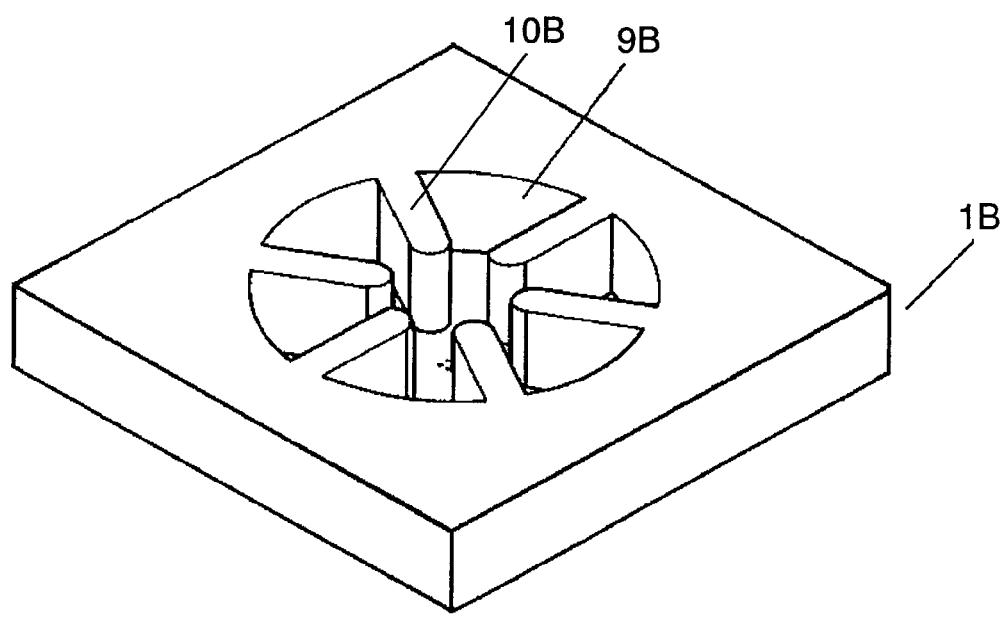
FIG. 10 is a perspective view of a sensing element used in the device of FIG. 1.

Wall 10B well 9B may be formed instead in a radial pattern which is directed towards the center, as shown in FIG. 10. The radial pattern of wall 10B facilitates homogeneous mixing of the dispensed drug with culture solution 22 kept in well 9B, even when a low dispensing pressure is injected for the drug and the speed of inflow is low. Sensing element 1B having radial wall 10B offers the same advantages as those offered by the spiral wall. Spiral-shaped wall 10A, or radial-shaped wall 10B, functions as a guide section for guiding drug into well 9A, or 9B, in the same manner as the bowl-shaped wall 10.

Size of depression 4 may be changed depending on subject cell 21; any size would do for the depression 4 in so far as it can retain cell 21 within depression 4. Typical dimensions for depression 4 are; 10-500 micron for the diameter, 1-500 micron for the depth. 10-100 micron for the diameter and 2-100 micron for the depth are preferable. More preferred dimensions for depression 4 are; 20 micron for the diameter and 10 or 20 micron for the depth.

Size of throughhole 3 may also be changed depending on subject cell 21, like the case with depression 4. Any size would do for the size of throughhole 3 in so far as it can retain cell 21 within depression 4. Typical dimensions for throughhole 3 are; 5-100 micron for the diameter, 10 nanometer-100 micron for the depth. 5 micron for the diameter and 1.5 micron for the depth are preferable.

Now in the following, a method of measuring extracellular potential using device 51 is described.

Drug is dispensed via tube 11 into culture solution 22 kept in case 2. The drug permeate within culture solution 22, and to the neighborhood of cell 21 held at depression 4.

When cell 21 is activated by the drug, the number of times of the ion exchange increases, during which ion exchange cell 21 takes such ions as $Na^+$, $K^+$, $Ca^{2+}$, etc. in and out through an ion channel within cell membrane (not shown). The ion exchange is an electrochemical change caused by cell 21 reacting to the drug.

The increased frequency of ion exchange causes the ion concentration within culture solution 22 to change at the neighborhood of cell 21, or in the inside of throughhole 3, which results in a change in the potential. Meanwhile, culture solution 22 inside of throughhole 3 normally has electrical resistance of 5 mega ohm or higher, and isolated from culture solution 22 kept in case 2. Therefore, change in the ion concentration or in the potential taking place in the inside of throughhole 3 can be picked up by detective electrode 8 in the form of an electrical signal.

The frequency of ion exchange taking place between cell 21 and culture solution 22 varies depending on a kind of cell 21. As a general rule, however, phenomenon of the ion exchange is not synchronized with a certain specific cycle, but it is considered that it is performed at respective ion channels with a certain probability. Namely, the electrical signals are observed not at a certain specific frequency alone, but frequency of the detected signals ranges widely, from DC level to approximately 5 kHz. The electrical signals generated by cell 21 have random frequency characteristics.

Figure 11:
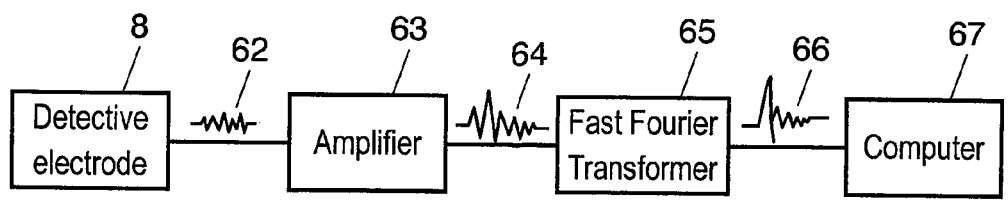
FIG. 11 is a chart showing a flow of measuring extracellular potential in the device of FIG. 1.

FIG. 11 shows the flow of an extracellular potential measurement. Electrical signal 62 is detected at detective electrode 8, a sensing section, as voltage or current. Detected electrical signal 62 is amplified by amplifier 63. Amplified electrical signal 64 is accumulated at fast Fourier transformer (FFT) 65 for a certain time to perform frequency domain changing. Signal strength 66 at the frequency domain is indicated by computer 67 at a certain specific interval. In this way, electrical signal 62 measured at detective electrode 8 is underwent the frequency changing, and then indicated and visualized by a computer.

Noise from outside has a regular frequency characteristic. Therefore, an electrical signal generated by cell 21 can be visually distinguished from the noise through the analysis of signal strength 66 at the frequency domain. So, even if there are noises coming from external power source, etc., the electrical signal generated from cell 21 can be easily distinguished from the noises, and recognized. Thus, a method of measuring extracellular potential in the present invention can catch accurately a change in the reaction of cell 21 caused by the drug.

Figure 12:
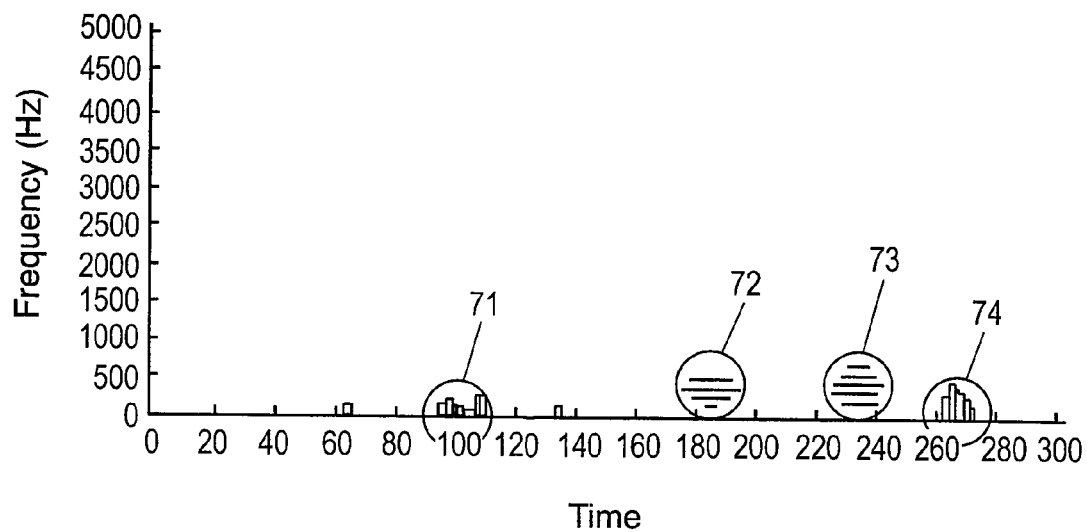
FIG. 12 is a characteristics chart of extracellular potential data measured using the device of FIG. 1.

FIG. 12 is a characteristics chart showing measurement data made available through an extracellular potential measuring method. In FIG. 12, the horizontal axis exhibits the time of measurement in the unit of a second, while the vertical axis exhibits the frequency. And, the signal strengths at the time of measurement are plotted in density (contour chart). Referring to FIG. 12, signal 72 and signal 73 show horizontal lines. This means that signal 72 and signal 73 have regular frequency characteristics; namely, these signals are noises coming from an external power supply or the like sources. Signal 71 and signal 74 don't have such regular frequency characteristics, which means that these signals are the electrical signals generated due to changes in the ion concentration in the neighborhood of cell 21.

Figure 14:
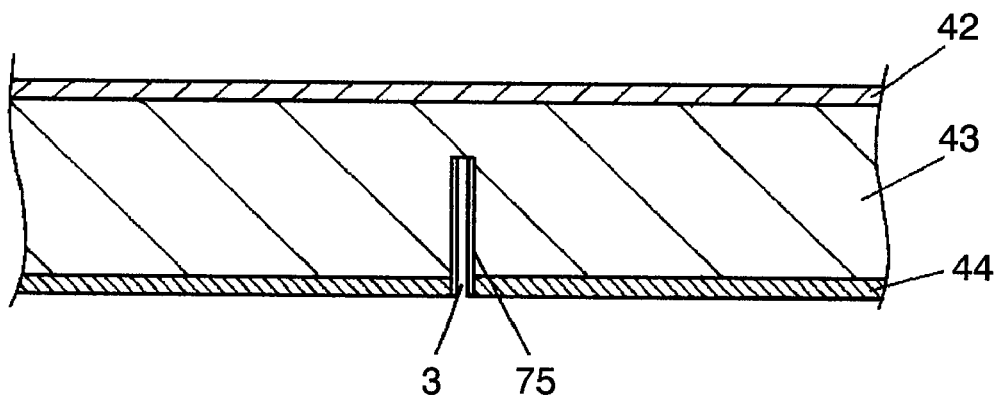
FIG. 14 is a partially magnified cross sectional view used to show a method of manufacturing the device of FIG. 1.
Figure 15:
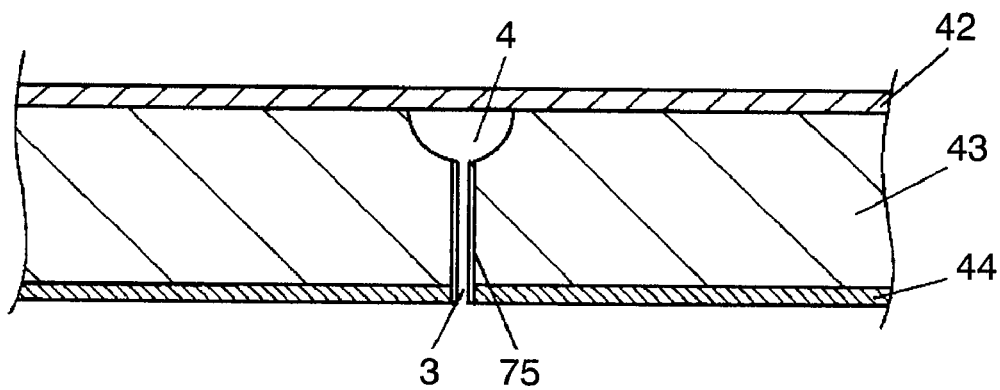
FIG. 15 is a partially magnified cross sectional view used to show a method of manufacturing the device of FIG. 1.

Next, a method of manufacturing extracellular potential measuring device 51 in accordance with a first exemplary embodiment is described. FIG. 13 and FIG. 16 through FIG. 20 show cross sectional views of sensing element 1 used to describe a method of manufacturing extracellular potential measuring device 51. FIG. 14 and FIG. 15 are magnified cross sectional views showing part of sensing element 1 used to describe a method of manufacturing extracellular potential measuring device 51. FIG. 21 is a cross sectional view used to describe a method of manufacturing extracellular potential measuring device 51.

Figure 13:
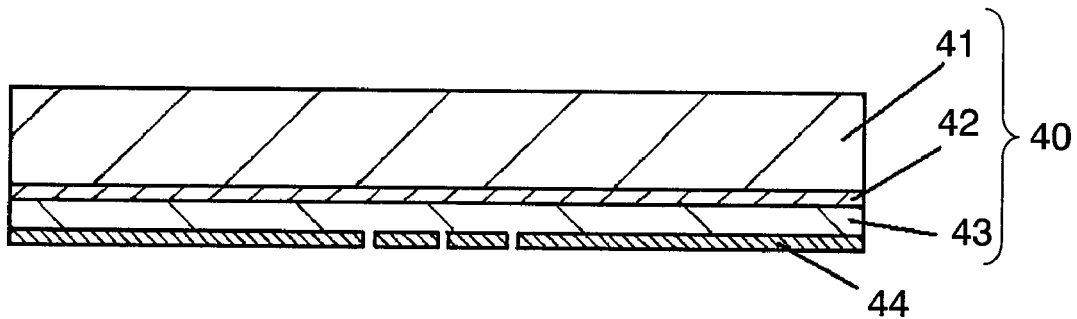
FIG. 13 is a cross sectional view used to show a method of manufacturing the device of FIG. 1.

As FIG. 13 illustrates, substrate 40 has a laminated body formed of base 41, intermediate layer 42 and thin plate 43. Base 41 and thin plate 43 are made of silicon, while intermediate layer 42 is made of silicon dioxide. Resist mask 44 having a certain specific pattern is provided on substrate 40 at the surface of thin plate 43 side with. The material for substrate 40 is generally called as SOI substrate, which substrate is often used for manufacturing the semiconductor devices. This means that the material is readily available anywhere, so description on the method of manufacturing substrate 40 is eliminated here.

In the first place, throughhole 3 is formed to thin plate 43 for a certain predetermined depth by dry etching process, as shown in FIG. 14. The most suitable process for providing throughhole 3 is dry etching process. In the dry etching method, a gas to accelerate the etching effect (accelerating gas) and a gas to retard the etching effect (retarding gas) are used (not shown). Typical accelerating gases are $XeF_2$, $CF_4$, $SF_6$. Typical retarding gases are $CHF_3$, $C_4F_8$. By using a mixture of accelerating gas and retarding gas for dry etching, wall surface of etched hole is covered with a protective layer, which is a polymer of $CF_2$. The protective layer formed covering the wall surface of a hole restrains etching against the wall surface. As the result, formation of throughhole 3 proceeds anisotropically only to the downward direction of resist mask 44.

The mechanism of anisotropic etching proceeding only in the downward direction is described more in detail.

Little etching advance with the acceleration gas in etching step. And then, formation of a protective layer by the retarding gas follows to provide a protective layer a little bit in protective layer forming step. In this way, the etching action and the formation of protective layer are repeated alternately; and a hole is etched in substantially the vertical direction and a protective layer is provided to cover the wall surface.

During the etching process, substrate 40 is placed in an atmosphere of plasma generated by inductive coupling of external coil. And a high frequency voltage is applied to substrate 40. In the above environment, the negative bias voltage arises in substrate 40, and the positive ion among the plasma, $SF_5^+$ or $CF_3^+$, collides against substrate 40. Thereby, the dry etching proceeds vertically down, and throughhole 3 is formed.

During the formation of protective layer, on the other hand, no high frequency voltage is applied to substrate 40. Then, no bias voltage is generated at substrate 40; so, the positive ion among plasma is not deflected, and the dry etching is retarded. A fresh new surface appeared as the result of etching action is exposed to the material for protective layer, $CF^+$. Consequently, the wall surface of throughhole 3 provided as the result of the dry etching is covered evenly with protective layer 75. In a dry etching experiment, $SF_6$ was used for the accelerating gas, $C_4F_8$ for the retarding gas, and formation of throughhole 3 and protective layer 75 has been confirmed.

As described in the above, when the dry etching procedure with the accelerating gas and the retarding gas is employed for providing throughhole 3, formation of the throughhole 3 proceeds in the depth direction of resist mask 44. Whereas, the retarding gas works to provide protective layer 75 covering the wall surface of throughhole 3.

Next, as shown in FIG. 15, it is dry etched using only $XeF_2$, or the like accelerating gas. Accelerating gas does not etch protective layer 75 formed on the wall surface of throughhole 3; the gas etches only the silicon surface at the bottom of throughhole 3. Since the acceleration gas does not etch silicon dioxide, intermediate layer 42 is not etched. As the result, depression 4 is formed for a size larger than throughhole 3.

Figure 16:
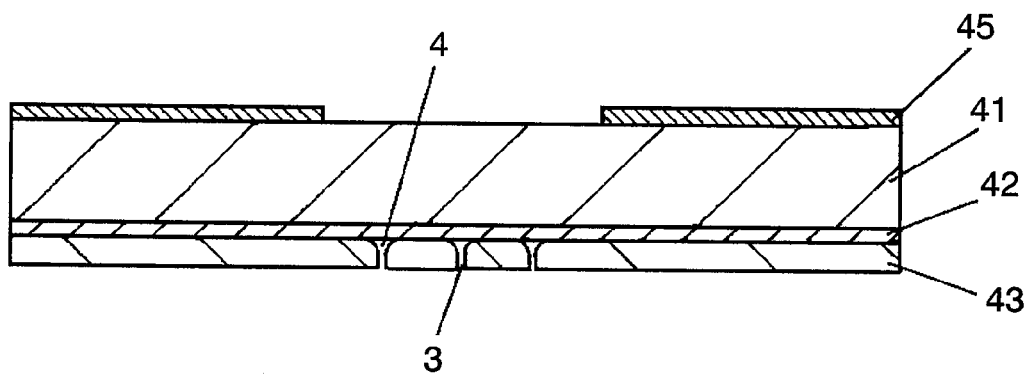
FIG. 16 is a cross sectional view used to show a method of manufacturing the device of FIG. 1.
Figure 17:
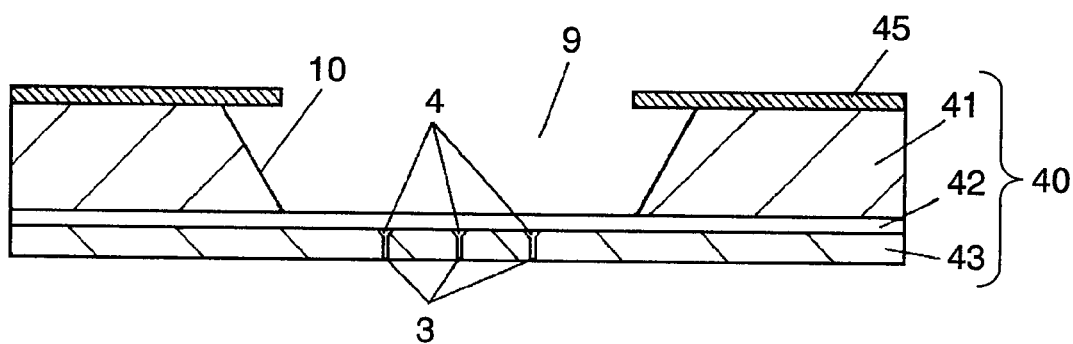
FIG. 17 is a cross sectional view used to show a method of manufacturing the device of FIG. 1.

Next, as shown in FIG. 16, it is etched using resist mask 45 provided on the surface at the base 41 side. This etching forms well 9 as illustrated in FIG. 17. The etching process employed for the formation of well 9 is a dry etching which uses only the accelerating gas, e.g. $XeF_2$, $SF_6$. Thereby, side wall 10 of well 9 is formed in a bowl shape.

For the purpose of forming well 9 in a spiral shape or a radial shape, dedicated etching masks are used respectively. The etching gas in this case contains the retarding gas too, besides the accelerating gas.

Figure 18:
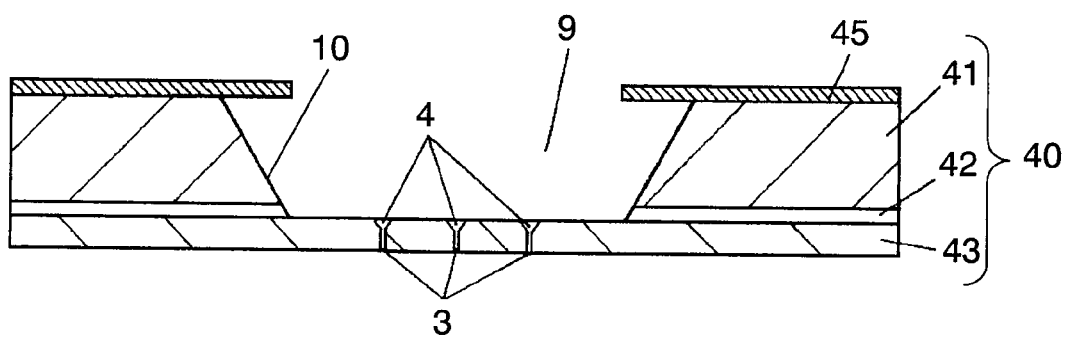
FIG. 18 is a cross sectional view used to show a method of manufacturing the device of FIG. 1.

Next, as shown in FIG. 18, intermediate layer 42 is etched off by a generally-used etching process, wet etching process or dry etching process.

Figure 19:
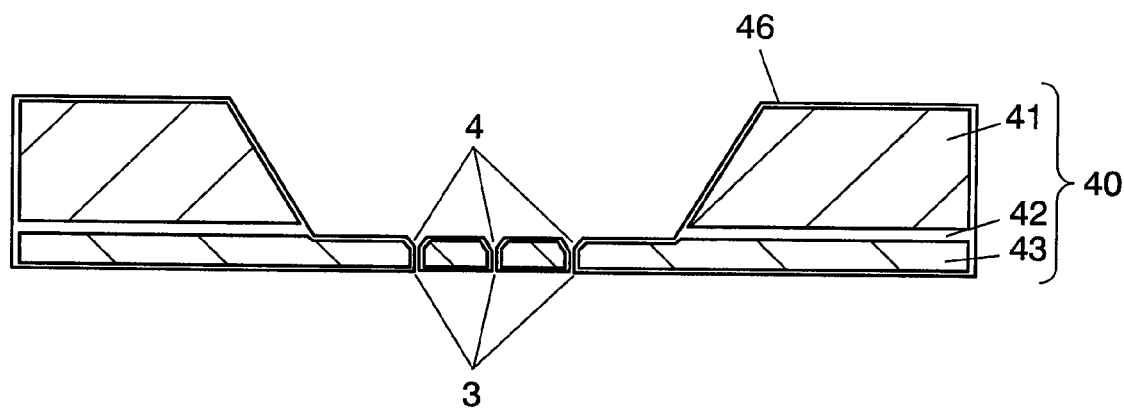
FIG. 19 is a cross sectional view used to show a method of manufacturing the device of FIG. 1.

And then, resist mask 45 is removed. Further, as shown in FIG. 19, oxide layer 46 is formed by a generally-used thermal oxidation process covering the silicon surface. Thermal oxidation process is employed in such cases where the surface resistance of silicon is requested to be as high as possible. In other cases where such a high surface resistance is not needed, a natural oxide layer formed on the silicon surface is enough.

Figure 20:
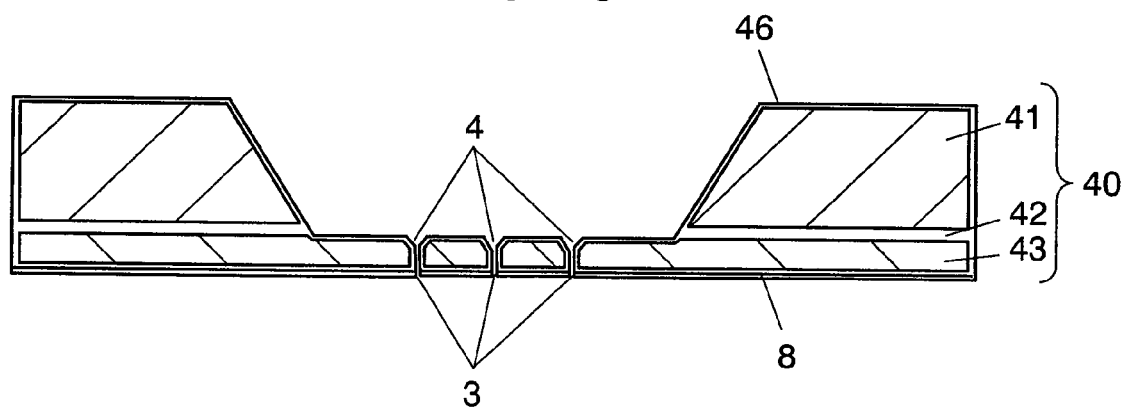
FIG. 20 is a cross sectional view used to show a method of manufacturing the device of FIG. 1.
Figure 21:
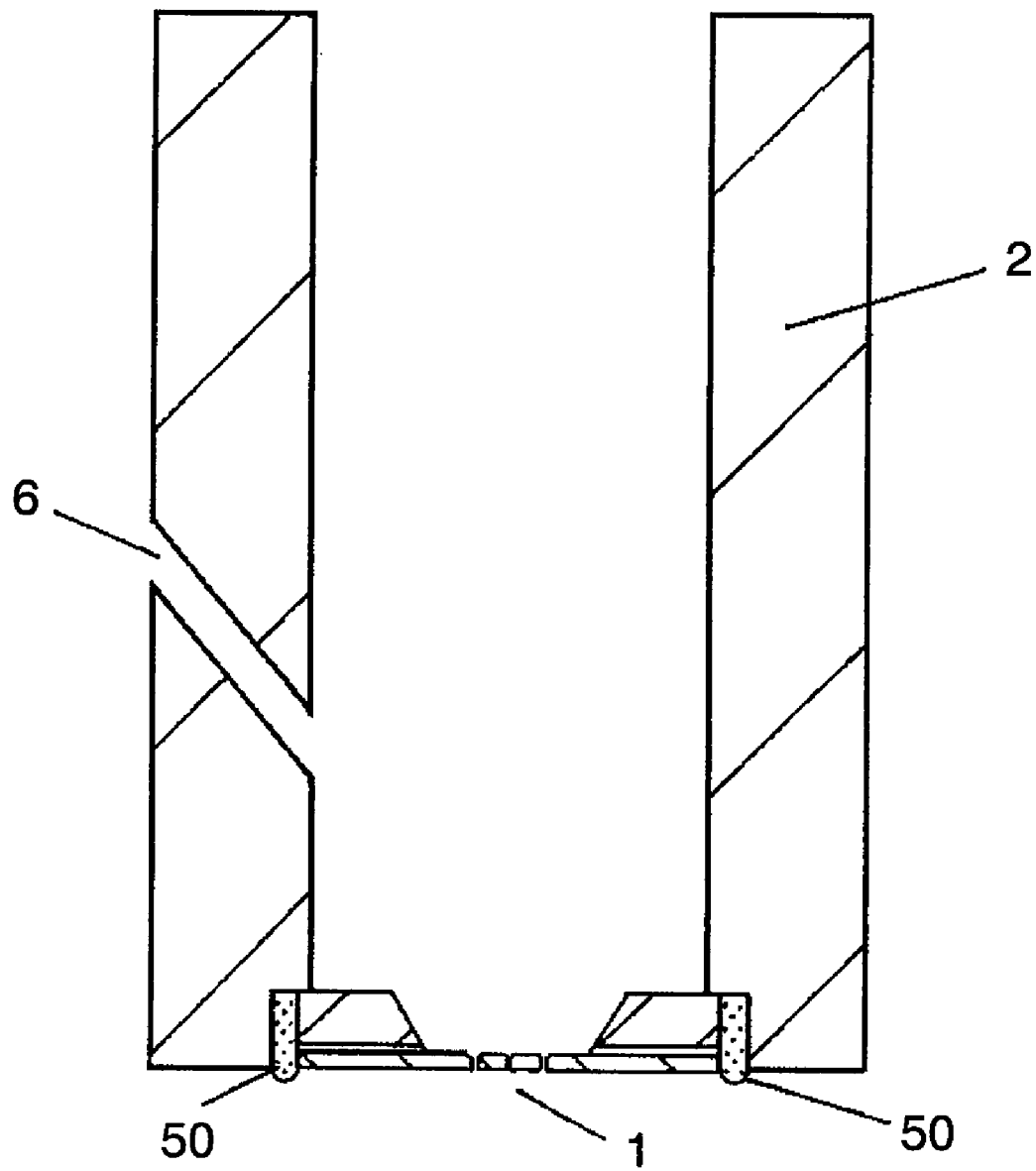
FIG. 21 is a cross sectional view used to show a method of manufacturing the device of FIG. 1.

Next, as shown in FIG. 20, substrate 40 is provided with detective electrode 8 formed on the surface of thin plate 43 side by a sputtering, a vacuum deposition or the like normal thin film formation process, using Au, Al, Ti, Cr, etc.

After processing substrate 40 by various process steps as described in the above, sensing element 1 is made. The use of a SOI substrate, which has a laminated body of silicon and silicon dioxide, for substrate 40 makes it possible to process the substrate at a high precision level through significantly simple and easy operations. Thus, sensing element 1 can be manufactured efficiently.

Finally, as shown in FIG. 21, sensing element 1 and case 2 are glued together using adhesive 50 or other means. Case 2 can be provided through a resin molding or other commonly-used processes; so, description on which is eliminated here. Case 2 should preferably be made of an electrically-insulating material so that culture solution 22 in case 2 does not suffer from an inadvertent change in the potential, and the measurement is not ill-affected.

Reference electrode 7 and tube 11 are inserted for conducting the measurement.

Although the above descriptions have been based on the use of laminated substrate 40 formed of silicon and silicon dioxide for sensing element 1, the material for intermediate layer 42 is not limited to silicon dioxide. Those other materials having the higher difficulty of etching in relation to silicon base 41 and thin plate 43, and provided with a high electrically-insulating property, may be used for intermediate layer 42. A glass material containing silicon dioxide, for example, can be use for intermediate layer 42.

Second Embodiment

Figure 22:
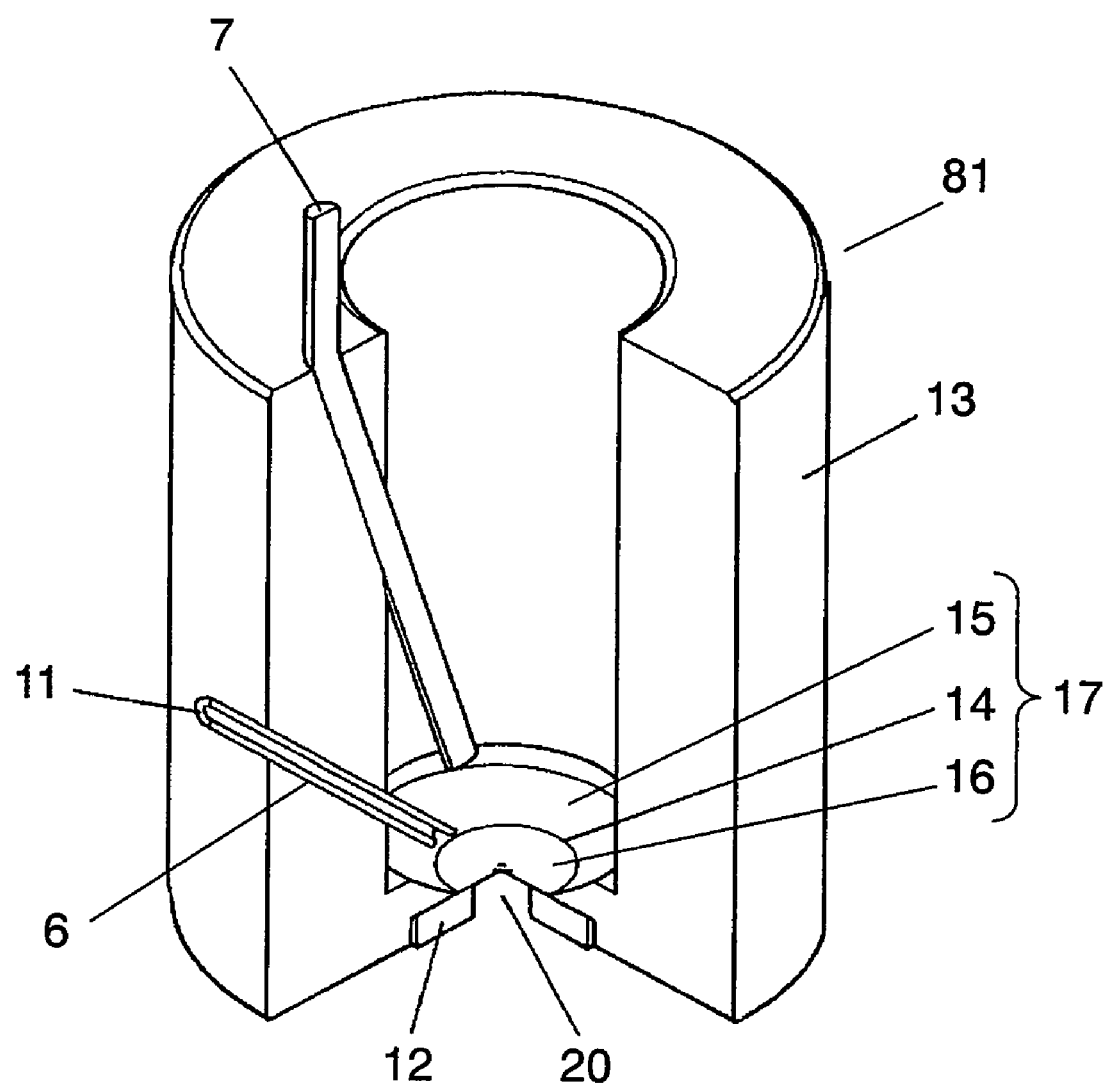
FIG. 22 is a partially-cut-off perspective view of an extracellular potential measuring device in accordance with a second exemplary embodiment.
Figure 23:
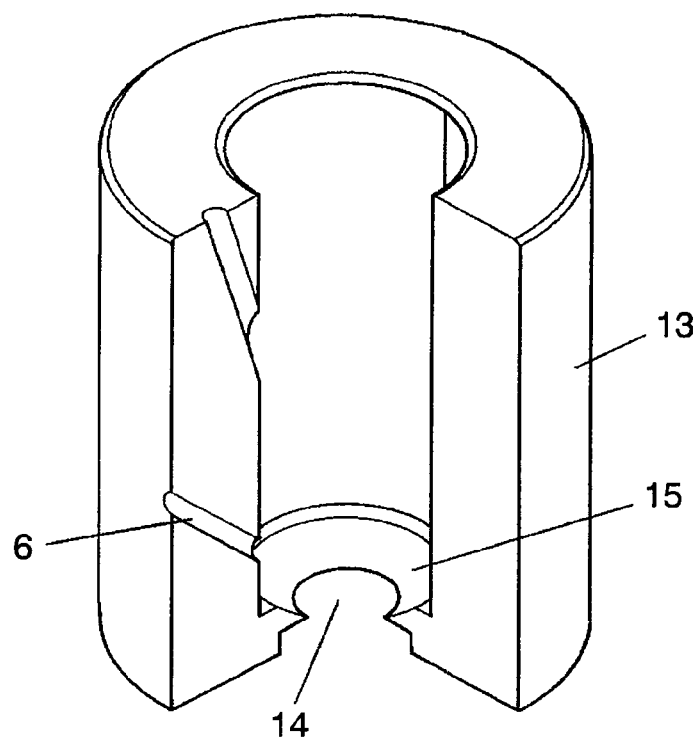
FIG. 23 is a partially-cut-off perspective view showing the device of FIG. 22.
Figure 24:
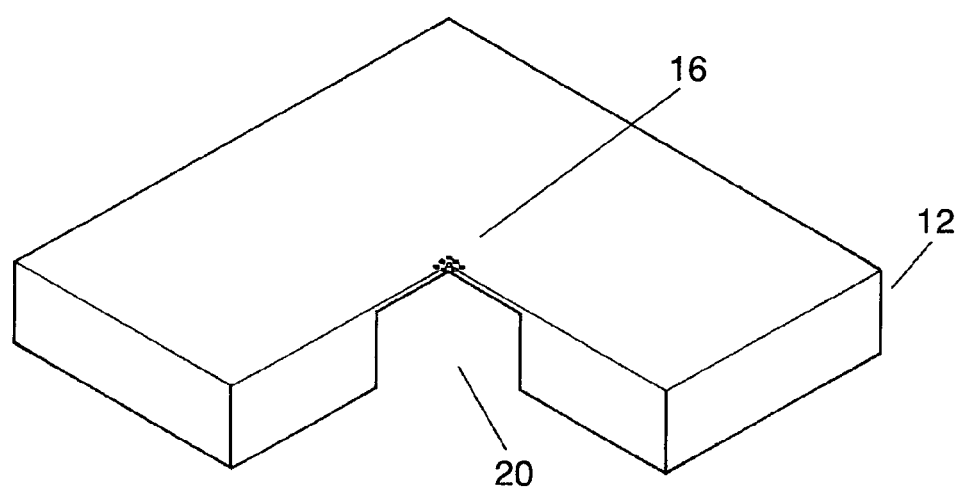
FIG. 24 is a partially-cut-off perspective view showing a sensing element used in the device of FIG. 22.
Figure 25:
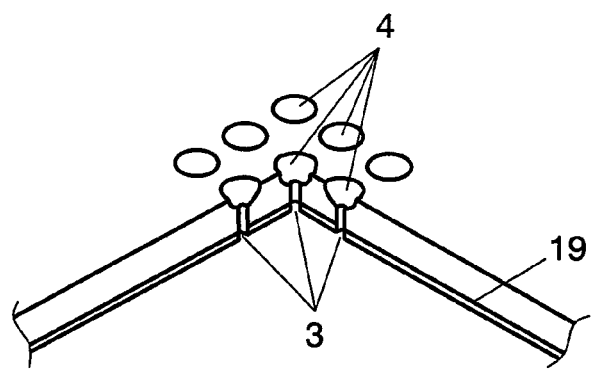
FIG. 25 is a partially-cut-off and magnified perspective view showing a key portion of the sensing element of FIG. 24.

Second exemplary embodiment of the present invention is described referring to FIG. 22 through FIG. 27. Those portions having the same structure as those of the first embodiment are indicated by using the same symbols. FIG. 22 is a partially cut-off perspective view of an extracellular potential measuring device in accordance with second embodiment. FIG. 23 is a partially cut-off perspective view of the case shown in FIG. 22. FIG. 24 is a partially cut-off perspective view of a sensing element. FIG. 25 is a magnified perspective view showing the sensing element of FIG. 24, with part of the element cut off.

Referring to FIG. 22, extracellular potential measuring device (device) 81 has been structured by attaching sensing element 12 to the bottom of case 13. Case 13 is made of an electrically-insulating resin material, and provided with reference electrode 7 which is set in the inside of the case for measuring a potential within case 13.

Sensing element 12 has a laminated body of silicon and silicon dioxide. Sensing element 12 has opening section 20 at the bottom part. Detective electrode 19 is placed at a lower surface of sensing element 12. The lower surface of sensing element 12 is formed by providing opening section 20. Sensing element 12 is provided at the upper surface with depression 4. First micro-throughhole (throughhole) 3 is formed penetrating through the bottom of depression 4 and the lower surface of sensing element 12 where detective electrode 19 is disposed.

Case 13 has second throughhole (throughhole) 14 at the bottom. Wall 15 of throughhole 14 is bowl-shaped. Well 17 is formed by upper surface 16 of sensing element 12 which is attached making contact with the bottom of case 13, throughhole 14 and wall 15. A point of difference from the first embodiment is in the structure of well 17.

Further, third throughhole 6 is provided in the side wall of case 13. On the assumption that sensing element 12 will be attached to the bottom of case 13, throughhole 6 is disposed in a radial direction that is coming from a certain specific place in the neighborhood of throughhole 3 and depression 4.

The method of using device 81 and the method of measuring extracellular potential using the device remain substantially the same as those methods in the first embodiment.

The bowl-shaped wall 15 ensures that the drug permeate to the neighborhood of subject cell 21 held in depression 4, even if flow speed for dispensing drug is slowed. Like in the first embodiment, there will be no change in the flow of culture solution 22 at the neighborhood of cell 21. So, the measuring environments can be kept stable. Namely, the bowl-shaped wall 15 works as a guide section for guiding the drug into a bottom of well 17.

Figure 26:
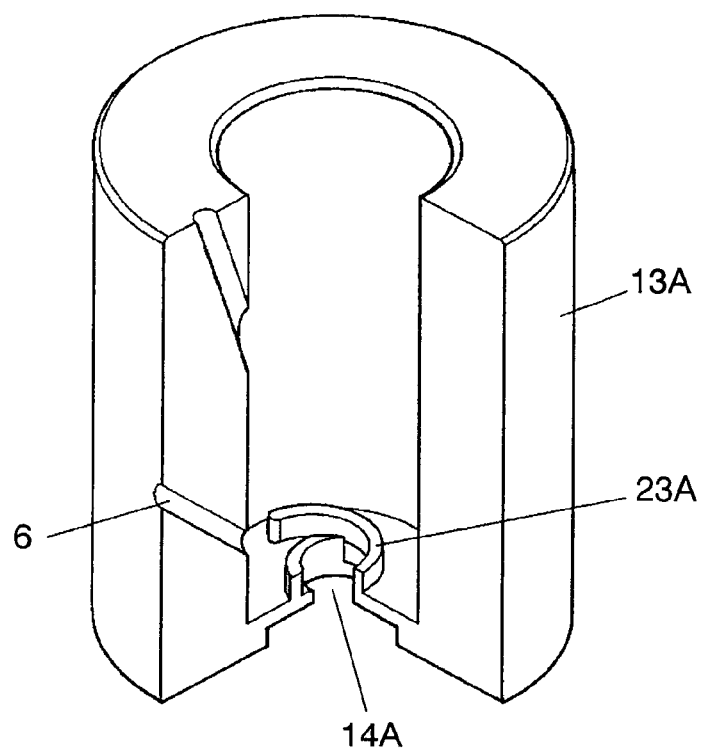
FIG. 26 is a partially-cut-off perspective view showing an extracellular potential measuring device in the present invention.

If wall 23A having a spiral-shape is provided at the bottom of case 13A, as shown in FIG. 26, orientated towards the center of throughhole 14A, drug dispensed into culture solution 22 are mixed homogeneously even if the inflow speed of drug is slowed a step further. Thus, wall 23A is advantageous for performing high accuracy measurements with less spread.

Figure 27:
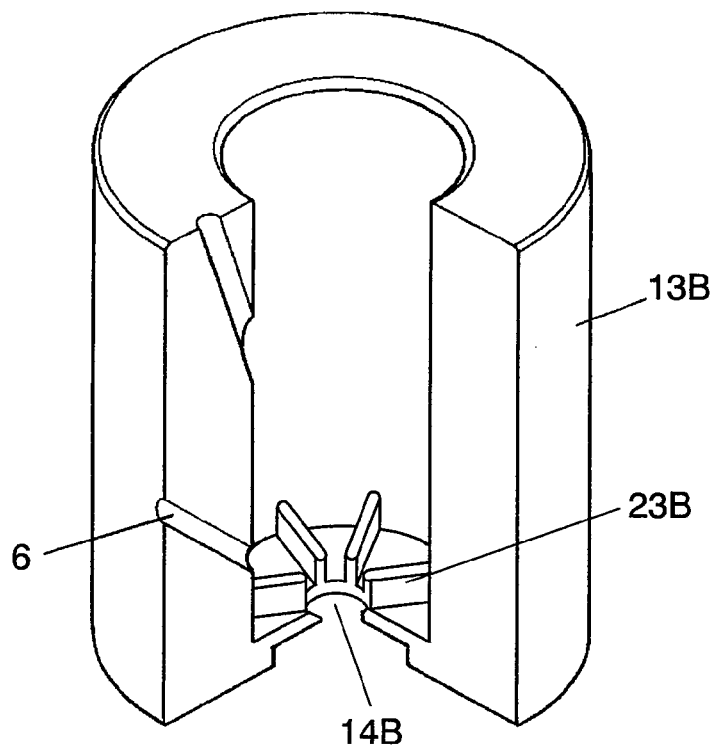
FIG. 27 is a partially-cut-off perspective view showing an extracellular potential measuring device in the present invention.

Further, as shown in FIG. 27, if wall 23B having a radial-shape orientated towards the center of throughhole 14B is provided at the bottom of case 13B, it provides the same advantage for performing the high accuracy measurements. Spiral-shaped wall 23A as well as radial-shaped wall 23B work as a guide section for guiding the drug into well 17, in the same manner the bowl-shaped wall 15 does.

Opening section 20 is not an essential item. In the present embodiment, opening section 20 has been provided for the purpose of producing good balance between a thickness of sensing element 12 needed for ensuring a sufficient mechanical strength and a depth of throughhole 3. Therefore, opening section 20 is not necessary if a thin sensing element 12 is rigid enough.

Next, a method of manufacturing extracellular potential measuring device 81 is described in accordance with second embodiment. FIG. 28 through FIG. 34 are cross sectional views of sensing element 12 used to show a method of manufacturing extracellular potential measuring device 81. FIG. 35 is a cross sectional view used to show a method of manufacturing extracellular potential measuring device 81.

Figure 28:
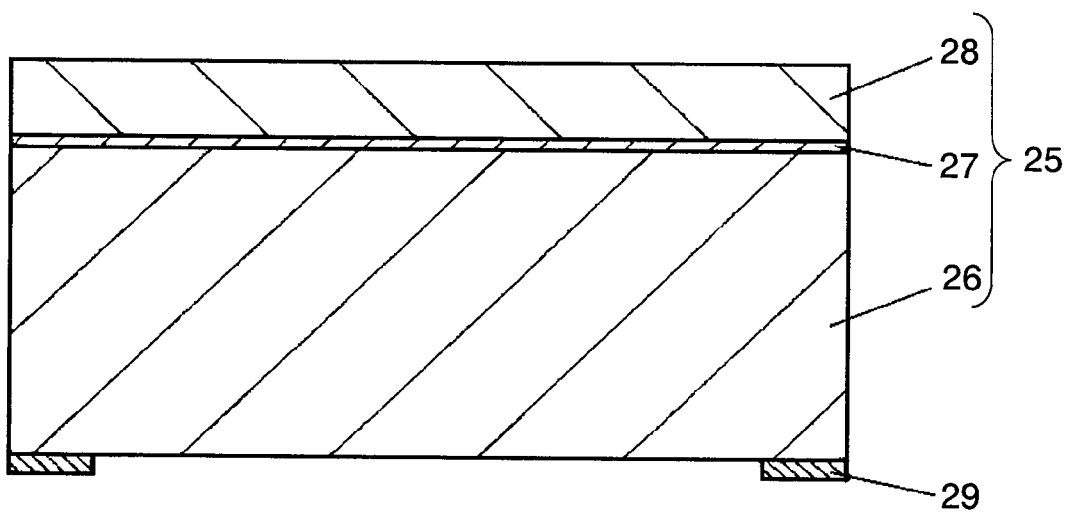
FIG. 28 is a partially magnified cross sectional view used to show a method of manufacturing the device of FIG. 22.

As shown in FIG. 28, substrate 25 is formed of base 26, intermediate layer 27 and thin plate 28. Material for both base 26 and thin plate 28 is silicon, while intermediate layer 27 is silicon dioxide. Substrate 25 is provided with resist mask 29 formed on the face of base 26 side. Substrate 25 is an SOI substrate, which is often used for manufacturing the semiconductor devices. This means that the SOI substrate is readily available anywhere, so, the method of manufacturing the substrate is eliminated here.

Figure 29:
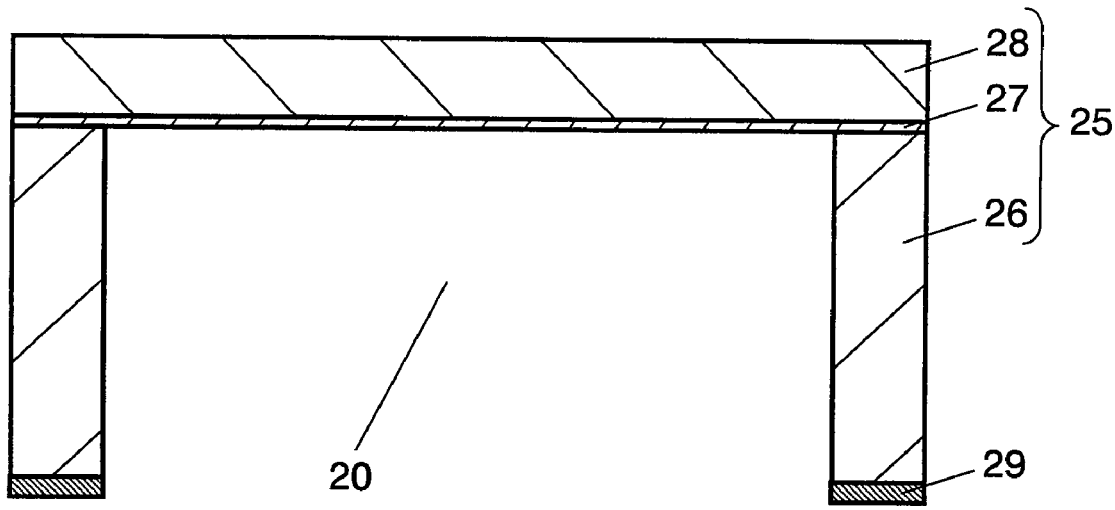
FIG. 29 is a partially magnified cross sectional view used to show a method of manufacturing the device of FIG. 22.

Base 26 is etched by a generally-used etching process, such as a dry etching or a wet etching, to form opening section 20, as shown in FIG. 29.

Figure 30:
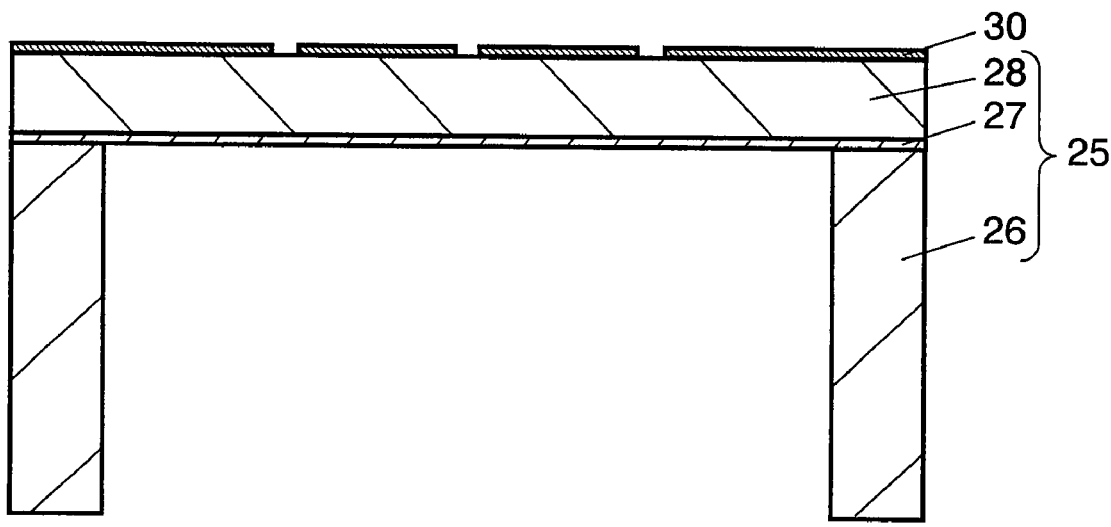
FIG. 30 is a partially magnified cross sectional view used to show a method of manufacturing the device of FIG. 22.

Next, as shown in FIG. 30, substrate 25 is provided with resist mask 30 of a certain specific pattern formed on the surface of thin plate 28.

Figure 31:
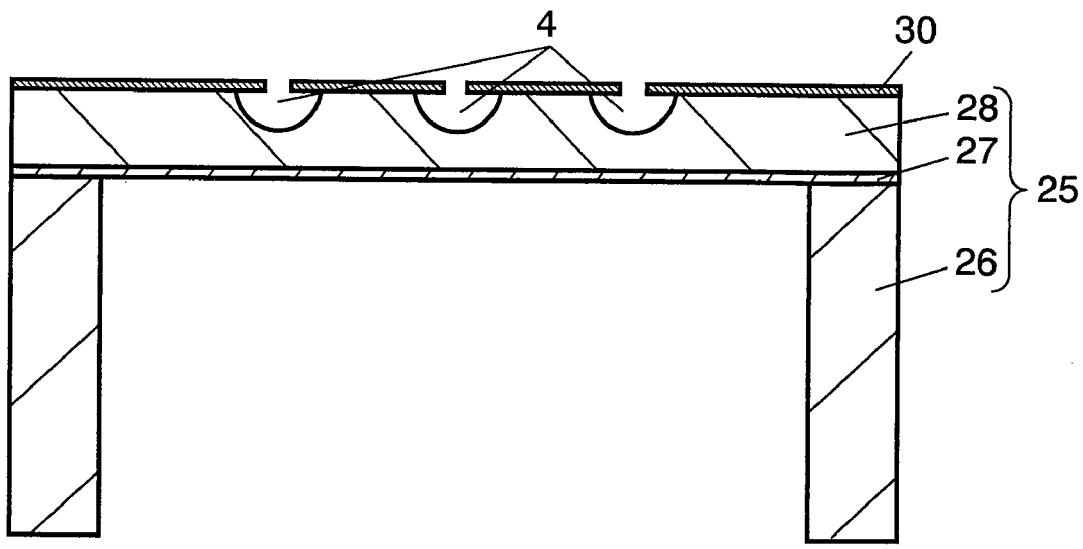
FIG. 31 is a partially magnified cross sectional view used to show a method of manufacturing the device of FIG. 22.
Figure 32:
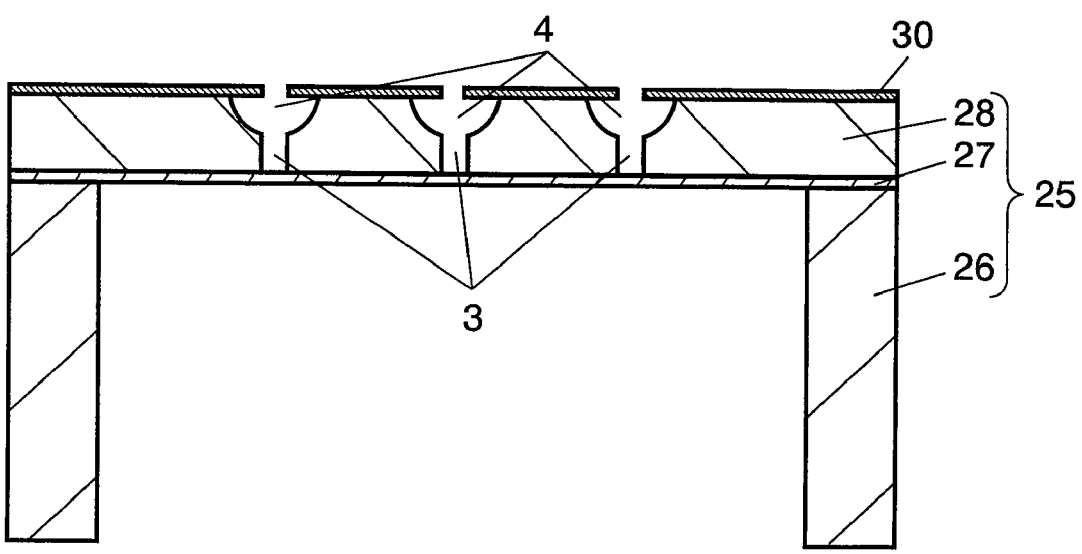
FIG. 32 is a partially magnified cross sectional view used to show a method of manufacturing the device of FIG. 22.

Then, as shown in FIG. 31, substrate 25 is dry-etched from the face of thin plate 28 side. The etching is conducted using only the accelerating gas. The accelerating gas used for the etching is $SF_6$, $CF_4$, $XeF_2$, etc. When silicon is etched by the accelerating gas, the etching proceeds not only in the direction of depth but it also advances towards width direction. This phenomenon has been confirmed in an experimental etching using $XeF_2$. Consequently, as shown in FIG. 31, the etching assumes a half-spherical shape concentric with the open area of resist mask 30, and depression 4 is formed. Since resist mask 30 is hardly etched by $XeF_2$, the mask maintains its original shape.

And then, as shown in FIG. 32, it is etched again from the face of thin plate 28 side, using a mixture of accelerating gas and retarding gas. Thereby, the etching proceeds anisotropically only in the vertically-down direction; so, throughhole 3 is formed starting at the bottom of depression 4.

Figure 33:
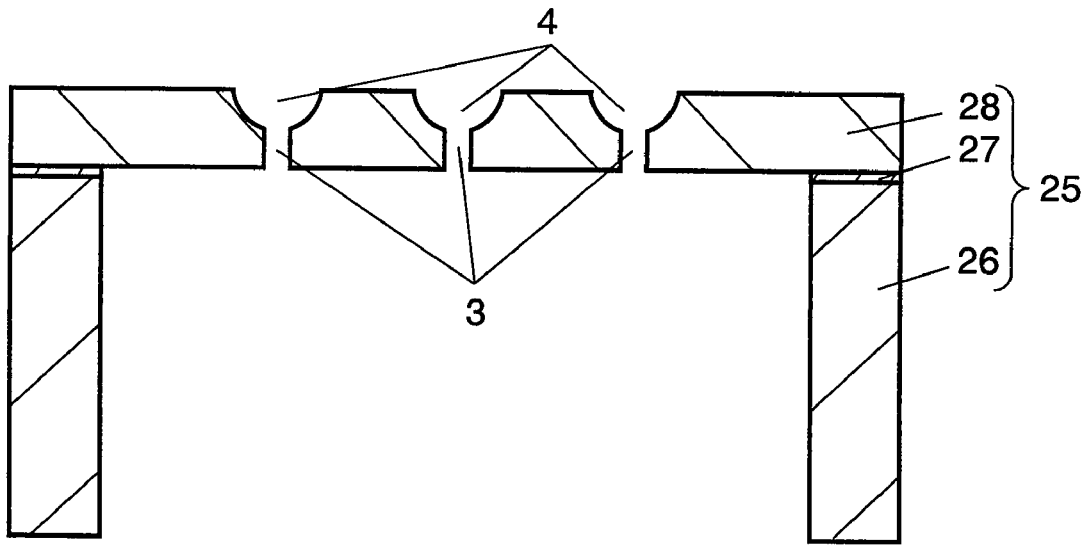
FIG. 33 is a partially magnified cross sectional view used to show a method of manufacturing the device of FIG. 22.

Next, as shown in FIG. 33, intermediate layer 27 made of silicon dioxide is etched off by a generally-used etching process, such as a wet etching, a dry etching, etc. from base 26 side. After then, resist mask 30 is also removed.

Figure 34:
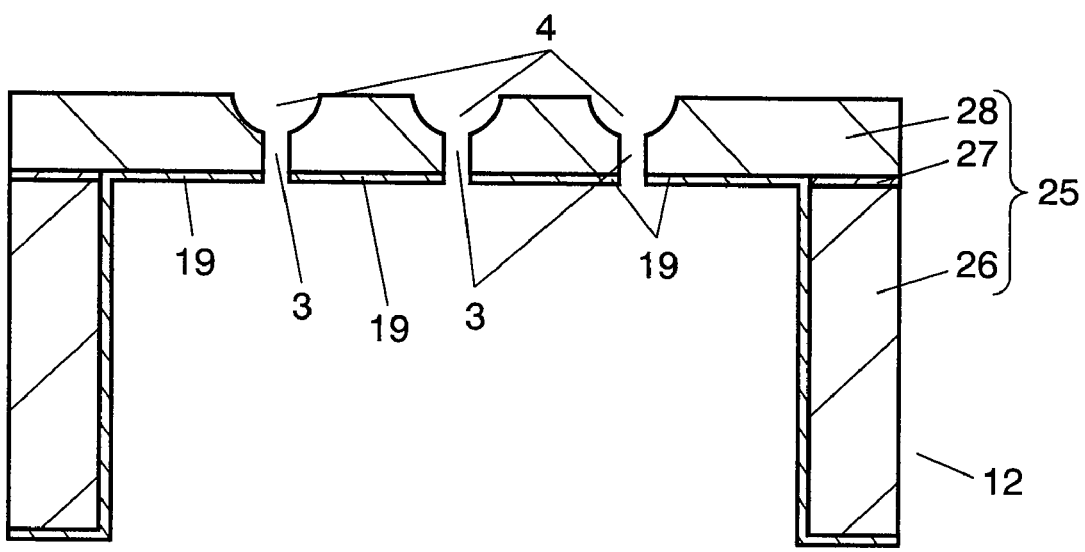
FIG. 34 is a partially magnified cross sectional view used to show a method of manufacturing the device of FIG. 22.
Figure 35:
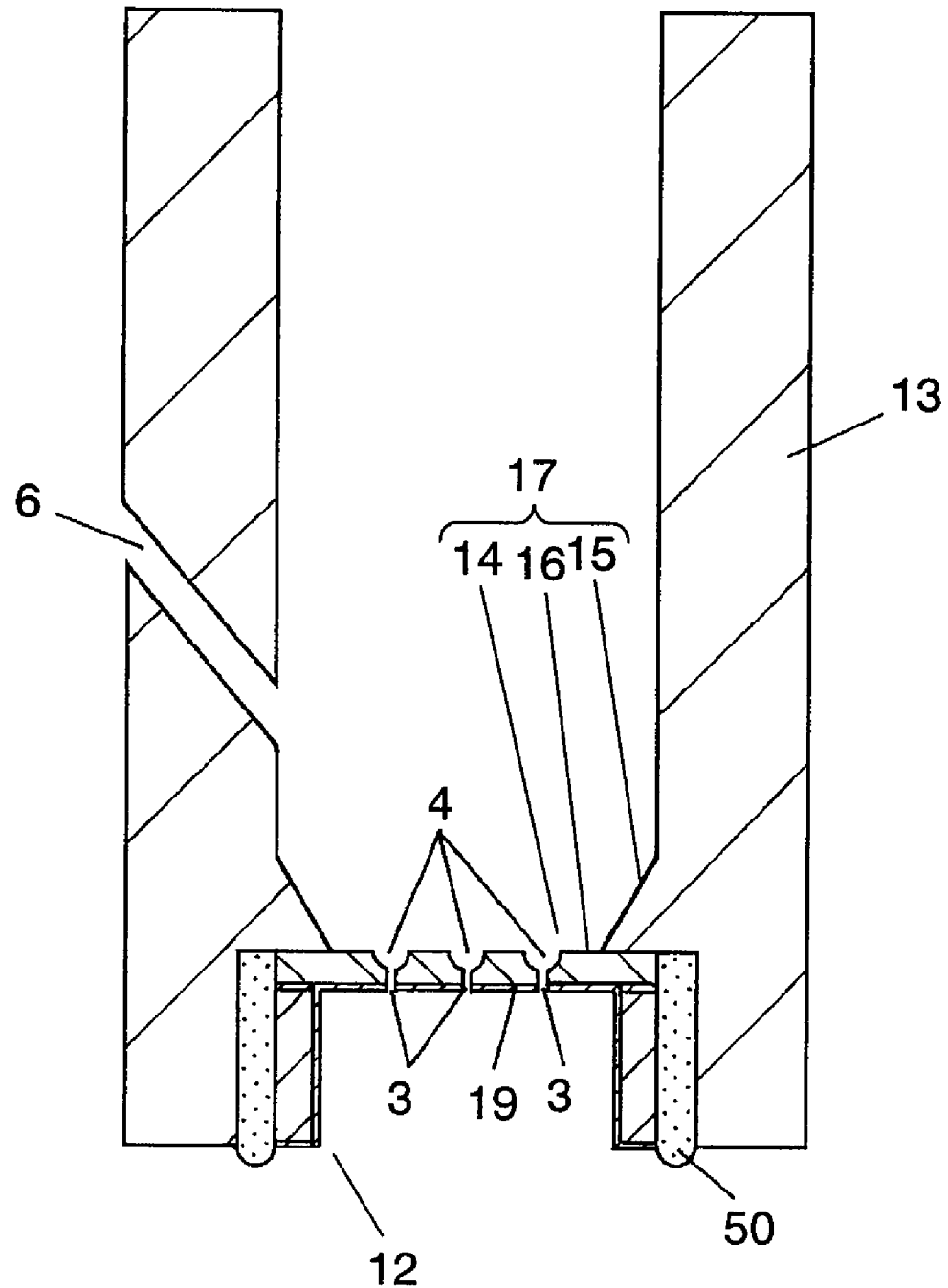
FIG. 35 is a cross sectional view used to show a method of manufacturing the device of FIG. 22.

Next, as shown in FIG. 34, substrate 25 is provided with detective electrode 19 formed on the face of base 26 side by a generally-used thin film forming technology using a material which contains Au as the main ingredient. Sensing element 12 is manufactured through the above described steps. Depending on needs, thermal oxidation process may be introduced prior to formation of detective electrode 19 in order to form oxide layer 46 covering the silicon surface.

Then, as shown in FIG. 35, sensing element 12 is glued, with the face of thin plate 28 side up, to the bottom of case 13 using adhesive 50 or other means, which case has already been manufactured separately with a resin material. Case 13 can be manufactured by a normally-used means such as a press molding, formation with optical means, cutting and machining, etc. Throughhole 14 at the bottom and throughhole 6 in the side wall of case 13 can be formed to a desired shape by making use of these technologies. There is no specific difficulty in the formation of throughhole 14 and throughhole 6; so, no description is made here on this point.

Extracellular potential measuring device 81 in the present second embodiment is thus manufactured.

Although the above descriptions have been based on the use of laminated substrate 25 formed of silicon and silicon dioxide for the manufacture of sensing element 1, the material for intermediate layer 27 is not limited to silicon dioxide. Other materials which have the higher difficulty of etching relative to silicon base 26 and thin plate 28, and are provided with a property of high electrical insulation may be used for intermediate layer 27. A glass material containing silicon dioxide, for example, can be use for intermediate layer 27.

Third Embodiment

Figure 36:
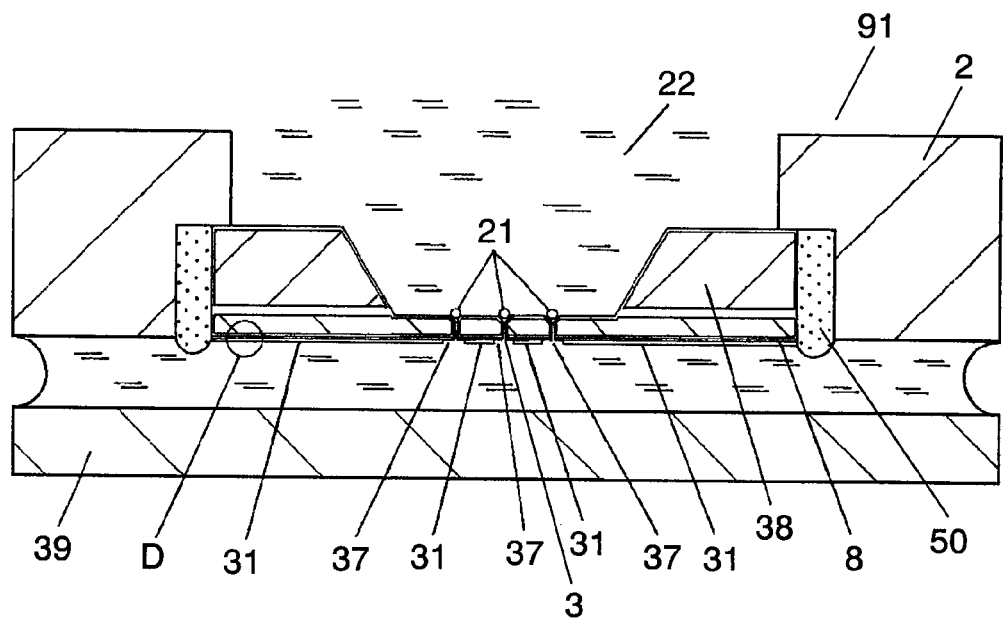
FIG. 36 is a partially-magnified cross sectional view showing an extracellular potential measuring device in accordance with a third exemplary embodiment.
Figure 37:
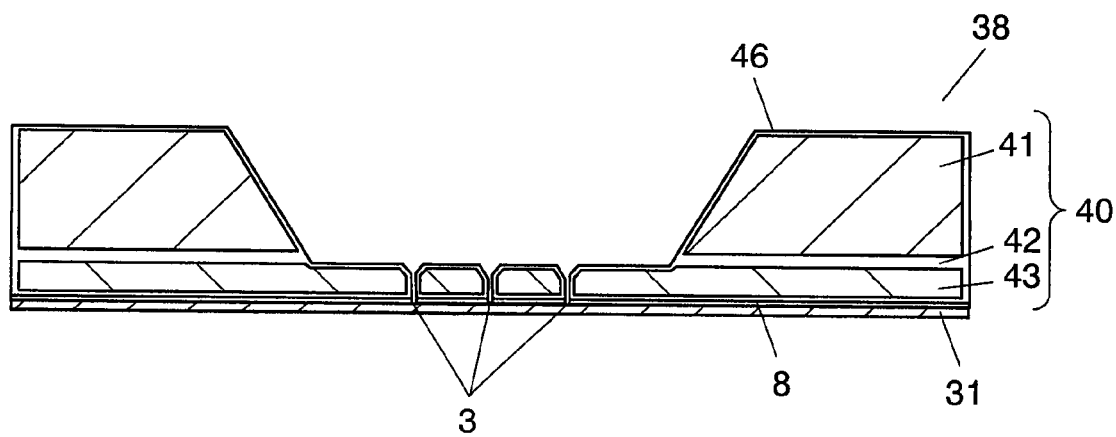
FIG. 37 is a partially-magnified cross sectional view showing a method of manufacturing the device of FIG. 36.
Figure 38:
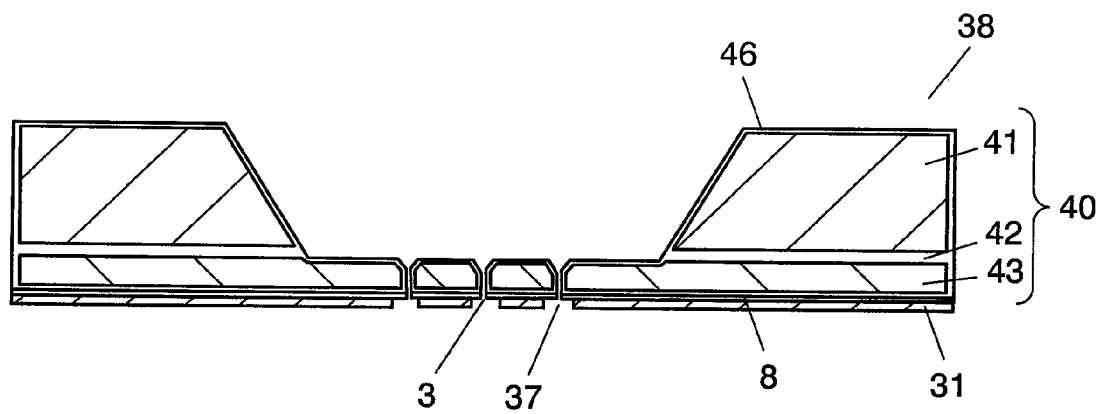
FIG. 38 is a partially-magnified cross sectional view showing a method of manufacturing the device of FIG. 36.

Third exemplary embodiment of the present invention is described referring to FIG. 36 through FIG. 38. Those portions having the same structure as those of the first embodiment are indicated by using the same symbols.

FIG. 36 is a cross sectional view showing the structure of an extracellular potential measuring device in accordance with third embodiment.

Those disclosed in the present third embodiment are applicable to the extracellular potential measuring device of first embodiment or second embodiment, and provide the same advantages.

The point of difference in third embodiment as compared with the first embodiment is that, as shown in FIG. 36 and FIG. 38, part of detective electrode 8 on sensing element 38 is covered with insulating layer 31. As the result, detective electrode 8 is exposed only at an area in the vicinity of throughhole 3. The exposed area of detective electrode 8 is opening section 37. Furthermore, insulating substrate 39 made of a glass material is provided to cover detective electrode 8 with a certain gap in between.

The procedure of detecting extracellular potential remains the same as in the first embodiment. So, no description is made on this respect. Here, the advantage of having insulating layer 31 on the surface of detective electrode 8 and the advantage of having insulating substrate 39 are described.

As already described in the first embodiment referring to FIG. 4 and FIG. 5, culture solution 22 flows out also into the detective electrode 8 side. Then, the flown out culture solution 22 makes contact with detective electrode 8 at the exposed area.

A region in which the ion concentration or the potential changes due to ion exchange of cell 21 is limited only to the region that is very close to cell 21. That is to say, the potential changes are limited only at the neighborhood of throughhole 3. However, the change in potential of culture solution 22 detected by detective electrode 8 is not limited to that taking place at the neighborhood of throughhole 3. For example, suppose the potential has changed in a region away from throughhole 3 (e.g. circled area C in FIG. 4) due to a noise which is irrelevant to activity of cell 21, detective electrode 8 detects the change of potential caused by the noise, either. Then, an electrical signal detected by detective electrode 8 represents the average of potential change due to ion exchange by cell 21 and that caused by noise. As the result, it is difficult to detect accurately only the potential change due to ion exchange by cell 21.

Therefore, as shown in FIG. 36, part of detective electrode 8 is covered with insulating layer 31, leaving only the limited area very close to opening section 37 exposed. Thereby, detective electrode 8 does not detect a change in the potential due to noise (e.g. a change taking place in the circled area D in FIG. 36). Thus the device yields stable measurement data without being affected by disturbing factors.

The smaller the exposed area of detective electrode 8, the less it is affected by noise; and stable measurement data are made available. For obtaining stable measurement results, an area of detective electrode 8 covered with insulating layer 31 should preferably be larger than an exposed area of detective electrode 8.

Furthermore, insulating substrate 39 suppresses the fluctuation with culture solution 22 at the detective electrode 8 side; hence, it reduces noise due to the fluctuation with culture solution 22. Namely, in device 51 of FIG. 4, culture solution 22 at the detective electrode 8 side is exposed to the atmospheric air So, if it is affected by an external vibration or if the atmospheric pressure changed during a measuring operation, culture solution 22 may sometimes cause fluctuation at the surface. The fluctuation at the surface generates a stream within culture solution 22. Then, a stream is generated also in culture solution 22 at the neighborhood of throughhole 3. This can lead to a noise. Therefore, it is difficult for detective electrode 8 to measure accurately the change in the ion concentration or in the potential due to ion exchange by cell 21.

Still further, a change of pressure occurred at the neighborhood of throughhole 3 may sometimes give influence to a pressure of holding cell 21. When cell 21 encounters a pressure change, an electrical insulation resistance separating throughhole 3 from case 2 also changes. At the same time, cell 21 changes its own state of electrical activity when cell 21 is exposed to a pressure change. Electrical signal detected at detective electrode 8 changes depending on a change in the insulation resistance or a change in cell 21's own state of electrical activity. As the result, it is difficult to measure accurately a change of the potential due to ion exchange which is caused by cell 21 reacting to the drug.

In the present embodiment, insulating substrate 39 is provided making contact to the surface of detective electrode 8 with a certain gap in between, as shown in FIG. 36. Culture solution 22 flown out into the detective electrode 8 side is confined between sensing element 38 and insulating substrate 39; therefore, the culture solution 22 is not exposed directly to the atmospheric air. So, it is least influenced by external forces. Even if an external vibration or a change in the atmospheric pressure takes place during a measuring operation, fluctuation will not arise with the surface of culture solution 22.

Thus, measuring device 91 detects extracellular potential accurately with a good stability. In order not to bring the potential of culture solution 22 into an inadvertent instability, it is preferred that insulating substrate 39 is made of an electrically-insulating material.

Now in the following, a method of manufacturing device 91 is described in accordance with third embodiment. Since the present third embodiment uses substrate 40 whose manufacturing method has already been described in the first embodiment, the manufacturing process steps described in the first embodiment (FIG. 13-FIG. 20) are not repeated here.

In the first place, substrate 40 as shown in FIG. 20 is prepared, which has been already provided with detective electrode 8 formed thereon. Then, as shown in FIG. 36, substrate 40 is provided with insulating layer 31 formed on the face of detective electrode 8 side, with an electrically-insulating material sputtered, vacuum deposited or spin-coated thereon, or through other processes. Polyimide, fluororesin, silicon dioxide, etc. may be used for the electrically-insulating material.

Next, as shown in FIG. 38, unnecessary part of insulating layer 31 is etched off using a resist mask, or by other suitable method, to form insulating layer 31 in a certain specific pattern. Thus sensing element 38 is obtained, detective electrode 8 of which being exposed only in a limited area at the neighborhood of throughhole 3.

Then, sensing element 38 is glued, with the face of detective electrode 8 side down, to the bottom of case 2, using adhesive 50 or other means. And then, as shown in FIG. 36, insulating substrate 39 is glued to sensing element 38 at the face of detective electrode 8 side, with a certain specific gap secured in between. In order to ensure a high accuracy of measurement, it is preferred to use an insulating resin adhesive (not shown) for gluing insulating substrate 39.

Figure 39:
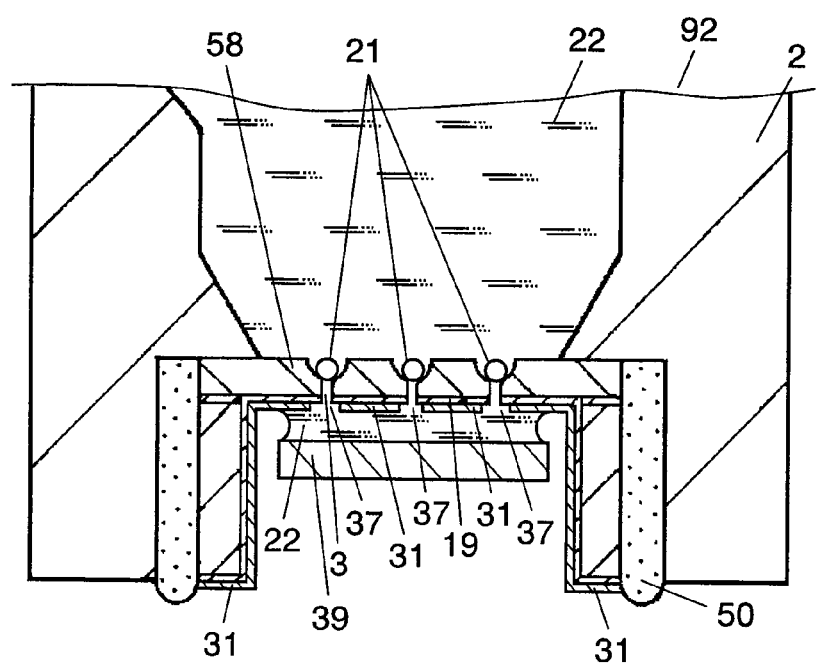
FIG. 39 is a partially-magnified cross sectional view showing an extracellular potential measuring device in accordance with a third exemplary embodiment.
Figure 40:
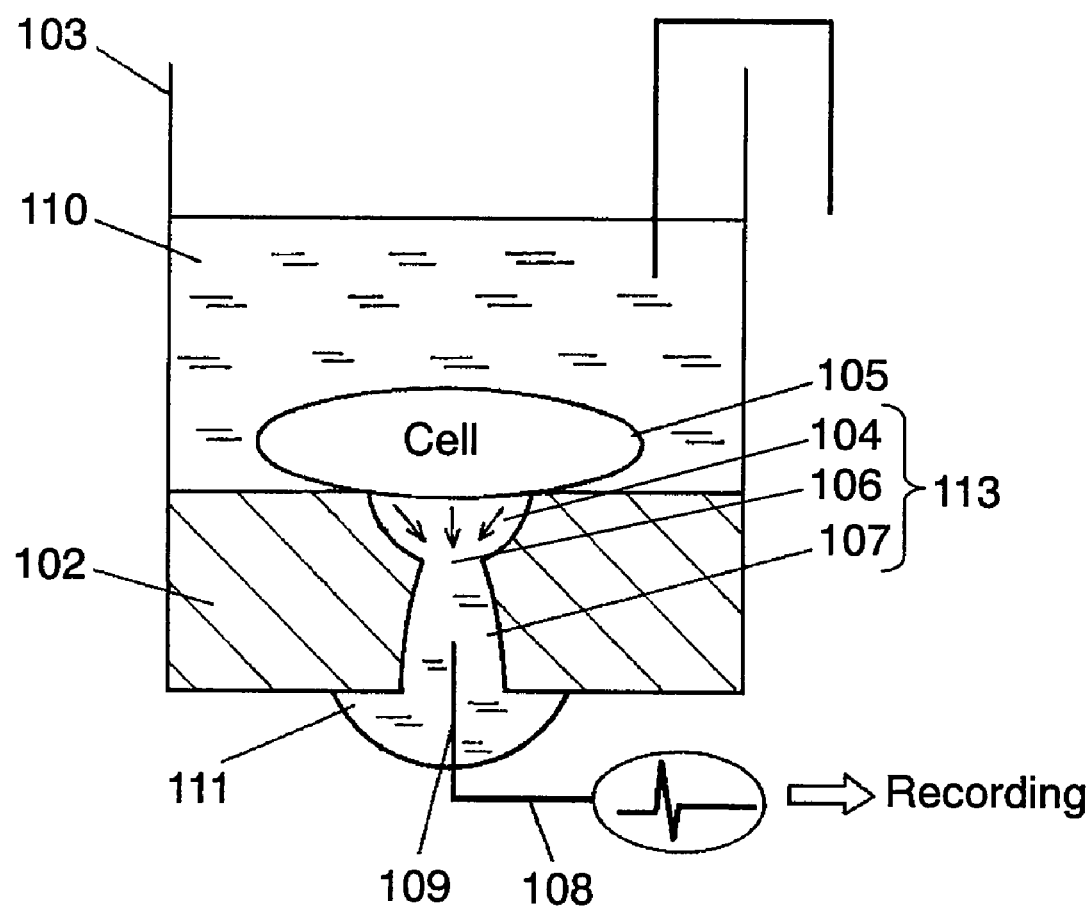
FIG. 40 is a cross sectional view showing a typified conventional extracellular potential measuring device.

The above-described configuration in third embodiment can be applied also to device 81 of the second embodiment. FIG. 39 is a partially-magnified cross sectional view showing extracellular potential measuring device 81 of the second embodiment, on which the configuration of third embodiment is applied.

The point of difference as compared with the second embodiment is that, as shown in FIG. 39, part of detective electrode 19 on sensing element 58 is covered with insulating layer 31. As the result, detective electrode 19 is exposed only at an area that is close to throughhole 3's opening section 37. Furthermore, insulating substrate 39 made of a glass material covers detective electrode 19 with a certain gap in between. The device exhibits the same functioning and advantages as described in the above.

In manufacturing extracellular potential measuring device 92, the same manufacturing method used for device 91 can be used.

What is claimed is:

1. An apparatus for measuring extracellular potential comprising:
   a sensing element including:
      a substrate;
      a well having a bottom and a wall, provided at the substrate for holding a subject cell, a culture solution and a drug together therein;
      a guide section provided on the wall for guiding the drug into the well and having a channel for mixing of the drug with the culture solution; and
      a detective electrode provided below the substrate, wherein
      a depression and a first throughhole penetrating through the depression and the lower surface of the substrate are provided at the bottom;
   a case contacting with the well and provided with a second throughhole penetrating through the case in a radial direction such that the second throughhole penetrates to the well to expose the depression;
   a tube inserted in the second throughhole, provided for dispensing either the culture solution or the drug into the case;
   an amplifier for amplifying an electrical signal detected at the detective electrode;
   a frequency transformer which acquires an electrical signal amplified by the amplifier and transforms the frequency; and
   a computer indicating an output signal frequency-transformed by the frequency transformer at a certain cycle.

2. The apparatus for measuring extracellular potential according to claim 1, wherein
   the substrate of the sensing element has an upper surface and a lower surface;
   the case is made of an insulating material having a third throughhole at the bottom, attached to make contact with the top of the sensing element;
   the guide section provided on a wall surface of the third throughhole, and
   the well is formed by the upper surface and the guide section.

3. The apparatus for measuring extracellular potential according to claim 2, wherein
   the guide section has one of a bowl shape, a spiral shape or a radial shape.

4. The apparatus for measuring extracellular potential according to claim 2, further comprising:
   an insulating layer covering part of the detective electrode.

5. The apparatus for measuring extracellular potential according to claim 4, wherein
   an area of the detective electrode covered by the insulating layer is greater than an exposed area of the detective electrode.

6. The apparatus for measuring extracellular potential according to claim 2, wherein
   the substrate has a laminated body formed of, silicon; and
   one material of silicon dioxide and a glass material containing silicon dioxide.

7. The apparatus for measuring extracellular potential according to claim 2, wherein
   the tube is made of one material of a resin, a glass and silica.

8. The apparatus for measuring extracellular potential according to claim 2, further comprising:
   an insulating substrate disposed opposed to the detective electrode with a gap in between.

9. The apparatus for measuring extracellular potential according to claim 1, wherein
   the guide section has one of a bowl shape, a spiral shape or a radial shape.

10. The apparatus for measuring extracellular potential according to claim 1, further comprising:
    an insulating layer covering part of the detective electrode.

11. The apparatus for measuring extracellular potential according to claim 10, wherein
    an area of the detective electrode covered by the insulating layer is greater than an exposed area of the detective electrode.

12. The apparatus for measuring extracellular potential according to claim 1, wherein
    the substrate has a laminated body formed of,
    silicon; and
    one material of silicon dioxide and a glass material containing silicon dioxide.

13. The apparatus for measuring extracellular potential according to claim 1, wherein
    the tube is made of one material of a resin, a glass and silica.

14. The apparatus for measuring extracellular potential according to claim 1, further comprising:
    an insulating substrate disposed opposed to the detective electrode with a gap in between.

* * * * *